(12) United States Patent
Kinsho et al.

(10) Patent No.: US 12,312,309 B2
(45) Date of Patent: May 27, 2025

(54) 3-ACYLOXYMETHYL-3-BUTENAL ACETAL COMPOUNDS

(71) Applicant: SHIN-ETSU CHEMICAL CO, LTD., Tokyo (JP)

(72) Inventors: Takeshi Kinsho, Niigata (JP); Akihiro Baba, Niigata (JP); Yusuke Nagae, Niigata (JP); Tomohiro Watanabe, Niigata (JP)

(73) Assignee: SHIN-ETSU CHEMICAL CO, LTD., Tokyo (JP)

( * ) Notice: Subject to any disclaimer, the term of this patent is extended or adjusted under 35 U.S.C. 154(b) by 0 days.

(21) Appl. No.: 18/371,276

(22) Filed: Sep. 21, 2023

(65) Prior Publication Data
US 2024/0067595 A1 Feb. 29, 2024

Related U.S. Application Data

(62) Division of application No. 17/833,170, filed on Jun. 6, 2022, now Pat. No. 11,897,842, which is a division of application No. 16/788,808, filed on Feb. 12, 2020, now Pat. No. 11,384,046, which is a division of application No. 15/825,299, filed on Nov. 29, 2017, now Pat. No. 10,611,718.

(30) Foreign Application Priority Data

Dec. 7, 2016 (JP) .............................. JP2016-237678

(51) Int. Cl.
| | | |
|---|---|---|
| C07C 67/40 | (2006.01) | |
| C07C 29/10 | (2006.01) | |
| C07C 29/14 | (2006.01) | |
| C07C 41/14 | (2006.01) | |
| C07C 41/30 | (2006.01) | |
| C07C 45/42 | (2006.01) | |
| C07C 45/45 | (2006.01) | |
| C07C 45/51 | (2006.01) | |
| C07C 67/03 | (2006.01) | |
| C07C 67/08 | (2006.01) | |
| C07C 67/14 | (2006.01) | |

(52) U.S. Cl.
CPC .............. *C07C 67/40* (2013.01); *C07C 29/10* (2013.01); *C07C 29/14* (2013.01); *C07C 41/14* (2013.01); *C07C 41/30* (2013.01); *C07C 45/42* (2013.01); *C07C 45/45* (2013.01); *C07C 45/515* (2013.01); *C07C 67/03* (2013.01); *C07C 67/08* (2013.01); *C07C 67/14* (2013.01)

(58) Field of Classification Search
CPC ......... C07C 47/21; C07C 67/40; C07C 29/10; C07D 317/12
USPC ....................................................... 560/129
See application file for complete search history.

(56) References Cited

U.S. PATENT DOCUMENTS

2018/0155267 A1 6/2018 Kinsho et al.

OTHER PUBLICATIONS

Knochel et al. Tetrahedron Lett. (1984), vol. 25, p. 1475-1478.*
Stoyanova et al., Godoshnik na Visshiya Khimikotekhnologicheski Institut, Sofiya (1991) 31 (2), 203-11.
Gieselmann, et al., J. Chem. Ecol., 5, 891 (1979).
Anderson, et al., Synthesis of 7-Methyl-3-Methylene-7-Octen-1-YL Propanoate and (Z)-3, 7-Dimethyl-2, 7-Octadien-1-YL Propanoate, Components of the Sex Pheromone of the San Jose Scale, Journal of Chemical Ecology, vol. 5, No. 5, pp. 919-927 (1979).
Anderson, et al., Synthesis and Identification of a Third Component of the San Jose Scale Sex Pheromone, Journal of Chemical Ecology, vol. 7, No. 4, pp. 695-706 (1981).
Alderdice et al., The Synthesis of the isomeric components of San Jose scale pheromone—an illustration of a , stereospecific synthesis of trisubstituted alkenes, Can. J. Chem. 71, pp. 1955-1963 (1993).
Lombardo, et al., Photoenolisation of Conjugated Esters: Synthesis of a San Jose Scale Pheromone by Partially Regio-Controlled Photochemical Deconjugation, Tetrahedron Letters, vol. 27, No. 46, pp. 5555-5558 (1986).
Zhang, et al., Modification of Wolinksy's Ene-Chlorination, Chinese Chemical Letters, vol. 2, No. 8, pp. 611-612 (1991).
Zhang, et al., Huaxue Tongbao, 40, (1994).
Yong, et al., Studies on the Alkylation of 3-Methyl-3-buten-1—01 Dianion: An Efficient Synthesis of 3-Methylene-1-alkanols Including a San Jose Scale Sex Pheromone, J. Org. Chem., 66, pp. 8248-8251 (2001).
Veselovskii, et al., Synthesis of a-Myrcenol Acetate and Propionate from Isobutenylcarbinol, Izvestiya Akademii Nauk SSSR, Seriya Khimicheskaya, 3,591, pp. 514-516 (1990).
Kreevoy et al. J. Am. Chem. Soc. 1955, 5590-5595.

* cited by examiner

*Primary Examiner* — Ana Z Muresan
(74) *Attorney, Agent, or Firm* — Williams Mullen; F. Michael Sajovec

(57) ABSTRACT

Provided is a 3-acyloxymethyl-3-butenal acetal compound of General Formula (10):

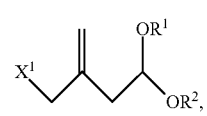

(10)

wherein $R^1$ and $R^2$, which may be the same or different, are each an alkyl group having 1 to 6 carbon atoms, or are bonded to each other to form a divalent alkylene group having 2 to 12 carbon atoms, and $X^1$ is an acyloxy group having 1 to 6 carbon atoms.

1 Claim, No Drawings

3-ACYLOXYMETHYL-3-BUTENAL ACETAL COMPOUNDS

RELATED APPLICATIONS

The following application is a divisional application of U.S. Non-Provisional application Ser. No. 17/833,170 filed Jun. 6, 2022, which is a divisional application of U.S. Non-Provisional application Ser. No. 16/788,808 filed Feb. 12, 2020, now U.S. Pat. No. 11,384,046, which is a divisional application of U.S. Non-Provisional patent application Ser. No. 15/825,299 filed Nov. 29, 2017, now U.S. Pat. No. 10,611,718, which claims priority to JP Application No. 2016-237678 filed on Dec. 7, 2016, which are all incorporated herein by reference in their entireties

BACKGROUND OF THE INVENTION

1. Field of the Invention

The invention relates to a 7-methyl-3-methylene-7-octenal acetal compound and methods for producing an aldehyde compound and an ester compound using the acetal compound.

2. Related Art 3,7-Dimethyl-2,7-octadienal and a corresponding alcohol, 3,7-dimethyl-2,7-octadienol are widely applied as floral perfumes and fruit flavors. Their regioisomers having double bonds at different positions, 7-methyl-3-methylene-7-octenal and 7-methyl-3-methylene-7-octenol, are expected to be applied in the same fields. Stoyanova et al. have reported that 7-methyl-3-methylene-7-octenal exists in the essential oil of seeds of Amomum tsaoko (Godoshnik na Visshiya Khimikotekhnologicheski Institut, Sofiya, 31, 203 (1991), CODEN: GVKIAH, ISSN: 0489-6211).

*Quadraspidiotus perniciosus* (generic name: San Jose Scale, hereinafter abbreviated as "SJS") is widely distributed in the world, damages fruit trees and ornamental trees, especially deciduous fruit trees, and thus is an economically critical insect pest. Gieselmann et al. and Anderson et al. have found that the sex pheromone of SJS contains three active components of 7-methyl-3-methylene-7-octenyl propionate, (Z)-3,7-dimethyl-2,7-octadienyl propionate, and (E)-3,7-dimethyl-2,7-octadienyl propionate (Gieselmann et al., J. Chem. Ecol., 5, 891 (1979), Anderson et al., J. Chem. Ecol., 5, 919 (1979), and Anderson et al., J. Chem. Ecol., 7, 695 (1981)).

An insect sex pheromone is a biologically active substance that is commonly secreted by female individuals to attract male individuals, and a small amount of the sex pheromone shows strong attractive activities. A sex pheromone has been widely used as means for forecasting insect emergence or for ascertaining regional spread (invasion into a specific area) and as means for controlling an insect pest. As the means for controlling the insect pest, control methods called mass trapping, lure and kill (another name: attract and kill), lure and infect (another name: attract and infect), and mating disruption are widely used in practice. To utilize a sex pheromone, it is necessary to economically produce a required amount of the sex pheromone product for basic research and also for application.

Synthetic examples of the SJS sex pheromones include the following Syntheses (a) to (f):

Synthesis (a): syntheses of 7-methyl-3-methylene-7-octenyl propionate and (Z)-3,7-dimethyl-2,7-octadienyl propionate by Anderson et al., containing addition of an organocuprate reagent to an alkyne as the key reaction (Anderson et al., J. Chem. Ecol., 5, 919 (1979));

Synthesis (b): syntheses of 7-methyl-3-methylene-7-octenyl propionate, (Z)-3,7-dimethyl-2,7-octadienyl propionate and (E)-3,7-dimethyl-2,7-octadienyl propionate by Weiler et al., containing a one-carbon homologation step from a β-keto ester compound: 7-methyl-3-oxo-7-octenoate (Weiler et al., Can. J. of Chemistry, 71, 1955 (1993));

Synthesis (c): synthesis of 7-methyl-3-methylene-7-octenyl propionate by Weedon et al., containing photochemical regioisomerization of a double bond from an α,β-unsaturated ester to a β,γ-unsaturated ester as the key reaction (A. C. Weedon et al., Tetrahedron Letters, 27, 5555 (1986));

Synthesis (d): synthesis of 7-methyl-3-methylene-7-octenyl propionate by Zhang et al. containing formation of exo-methylene as the key reaction through reduction of an allylic chloride obtained by chlorination involving isomerization of a trisubstituted double bond (H. S. Zhang et al., Chinese Chemical Letters, 2, 611 (1991), and Zhang et al., Huaxue Tongbao, 40, (1994));

Synthesis (e): synthesis of 7-methyl-3-methylene-7-octenyl propionate through alkylation of a dianion of 3-methyl-3-buten-1-ol by Anderson et al. and Chong et al. (Anderson et al., J. Chem. Ecol., 7, 695 (1981), and J. M. Chong et al., J. of Org. Chem., 66, 8248 (2001)); and Synthesis (f): non-selective synthesis of 7-methyl-3-methylene-7-octenyl propionate through an allylic chloride mixture by Veselovskii et al. (V. V. Veselovskii et al., Izvestiya Akademii Nauk SSSR, Seriya Khimicheskaya, 3, 591 (1990)).

SUMMARY OF THE INVENTION

In the report by R. Stoyanova et al., 0.58% of the essential oil of seeds of Amomum tsaoko is identified as 7-methyl-3-methylene-7-octenal by a mass spectrum. However, there is no description other than the mass spectrum. Synthesis of 7-methyl-3-methylene-7-octenal is not reported.

The conventional synthetic methods bring various difficulties to industrially produce SJS sex pheromone compounds at high yields. For example, the difficulties arise from the use of reagents that are expensive or difficult to handle on an industrial scale, including organolithium reagents such as n-butyllithium and methyllithium [Syntheses (b) and (e)], lithium aluminum hydride (LAH) [Syntheses (a), (b) and (d)], a stoichiometric amount of an organocuprate reagent [Synthesis (a)], a Tebbe reagent [Synthesis (b)], and sulfuryl chloride [Synthesis (f)]. In the photochemical isomerization with intentional double bond isomerization [Synthesis (c)], difficulties arise from formation of an undesired isomer as a by-product and its removal. In isomerization of another double bond [Syntheses (d) and (f)], significant difficulties arise because a target compound is difficult to separate from isomers thereof, thereby lowering the yield. In Syntheses (a) to (f), intermediates and a target compound are isolated or purified by various types of chromatography, which are difficult to perform on an industrial scale.

As described above, the conventional syntheses are considered to be very difficult to economically and industrially produce a sufficient amount of a sex pheromone product. Hence, an efficient production method capable of supplying a sufficient amount of a sex pheromone compound is industrially important.

The three components contained by the SJS sex pheromone composition have substantially the same attractive activity, and any one of the three components may be used in practical use. However, the future development of resistance for a long-term use can be considered to be suppressed by use of a mixture of the components derived from the insect rather than by single use of any one of the three components.

Hence, a method of producing all of the three components as the SJS sex pheromones from a common intermediate will eliminate the necessity of separately producing each of the three components. Such a method is of industrial significance.

As a result of intensive studies on a 7-methyl-3-methylene-7-octenal acetal compound (1) as a candidate of the common intermediate for solving the problem, the inventors have found that the compound (1) can be produced by an industrially easy and practical method. The inventors have also found that, from the intermediate, 7-methyl-3-methylene-7-octenal (2), a 7-methyl-3-methylene-7-octenyl carboxylate compound (4), 3,7-dimethyl-2,7-octadienal (5), a 3,7-dimethyl-2,7-octadienyl carboxylate compound (7), and a mixture of a 7-methyl-3-methylene-7-octenyl carboxylate compound (4) and a 3,7-dimethyl-2,7-octadienyl carboxylate compound (7) can be produced. The inventors have further found that a 3-acyloxymethyl-3-methylene-butenal acetal compound (10), which can be used to produce a 7-methyl-3-methylene-7-octenal acetal compound (1), has excellent storage stability. The inventors have completed the invention in this way.

In an aspect of the invention, there is provided a method for producing 7-methyl-3-methylene-7-octenal, comprising a step of hydrolyzing a 7-methyl-3-methylene-7-octenal acetal compound of General Formula (1) to obtain 7-methyl-3-methylene-7-octenal of Formula (2).

In another aspect of the invention, there is provided a method for producing a 7-methyl-3-methylene-7-octenyl carboxylate compound, comprising steps of: hydrolyzing a 7-methyl-3-methylene-7-octenal acetal compound of General Formula (1) to obtain 7-methyl-3-methylene-7-octenal of Formula (2); reducing the 7-methyl-3-methylene-7-octenal (2) to obtain 7-methyl-3-methylene-7-octenol of Formula (3); and esterifying the 7-methyl-3-methylene-7-octenol (3) to obtain a 7-methyl-3-methylene-7-octenyl carboxylate compound of General Formula (4).

In still another aspect of the invention, there is provided a method for producing 3,7-dimethyl-2,7-octadienal, comprising steps of: hydrolyzing a 7-methyl-3-methylene-7-octenal acetal compound of General Formula (1) to obtain 7-methyl-3-methylene-7-octenal of Formula (2); and isomerizing the 7-methyl-3-methylene-7-octenal (2) in the presence of a base to obtain 3,7-dimethyl-2,7-octadienal of Formula (5).

In a further aspect of the invention, there is provided a method for producing a 3,7-dimethyl-2,7-octadienyl carboxylate compound, comprising steps of: hydrolyzing a 7-methyl-3-methylene-7-octenal acetal compound of General Formula (1) to obtain 7-methyl-3-methylene-7-octenal of Formula (2); isomerizing the 7-methyl-3-methylene-7-octenal (2) in the presence of a base to obtain 3,7-dimethyl-2,7-octadienal of Formula (5); reducing the 3,7-dimethyl-2,7-octadienal (5) to obtain 3,7-dimethyl-2,7-octadienol of Formula (6); and esterifying the 3,7-dimethyl-2,7-octadienol (6) to obtain a 3,7-dimethyl-2,7-octadienyl carboxylate compound of General Formula (7).

In a still further aspect of the invention, there is provided a 7-methyl-3-methylene-7-octenal acetal compound of General Formula (1).

In an aspect of the invention, there is provided a method for producing a 7-methyl-3-methylene-7-octenal acetal compound, comprising a step of coupling a nucleophilic reagent expressed as a 3-methyl-3-butenyl M of General Formula (8) with an acetal compound of General Formula (9) to obtain a 7-methyl-3-methylene-7-octenal acetal compound of General Formula (1).

In an aspect of the invention, there is provided a 3-acyloxymethyl-3-butenal acetal compound of General Formula (10).

In another aspect of the invention, there is provided a method for simultaneously producing a 7-methyl-3-methylene-7-octenyl carboxylate compound and a 3,7-dimethyl-2,7-octadienyl carboxylate compound, comprising steps of: subjecting a 7-methyl-3-methylene-7-octenal acetal compound of General Formula (1) to hydrolysis and isomerization to obtain a first mixture of 7-methyl-3-methylene-7-octenal of Formula (2) and 3,7-dimethyl-2,7-octadienal of Formula (5), wherein an acid or a base is present in the isomerization; reducing the first mixture to obtain a second mixture of 7-methyl-3-methylene-7-octenol of Formula (3) and 3,7-dimethyl-2,7-octadienol of Formula (6); and esterifying the second mixture to obtain a third mixture of a 7-methyl-3-methylene-7-octenyl carboxylate compound of Formula (4) and a 3,7-dimethyl-2,7-octadienyl carboxylate compound of General Formula (7).

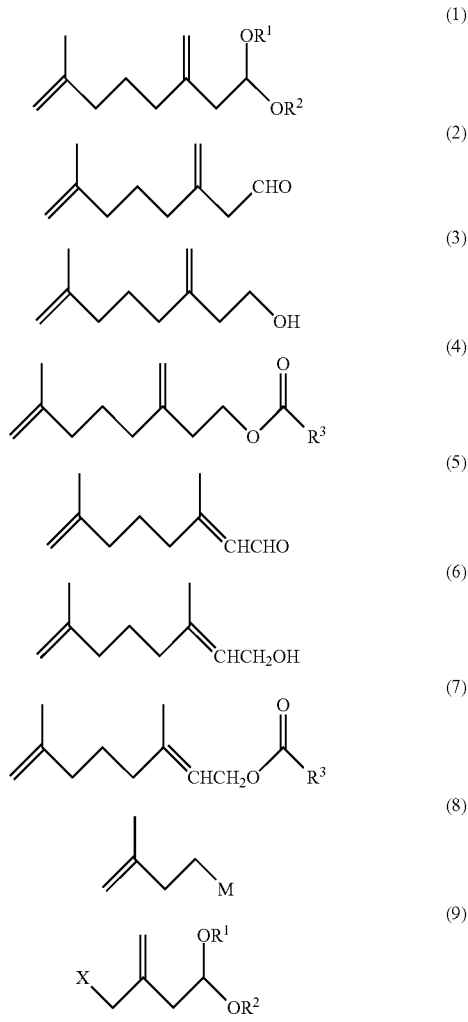

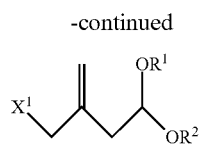
(10)

In the formulae, $R^1$ and $R^2$, which may be the same or different, are each an alkyl group having 1 to 6 carbon atoms, or are bonded to each other to form a divalent alkylene group having 2 to 12 carbon atoms; $R^3$ is a monovalent hydrocarbon group having 1 to 6 carbon atoms; M is a cationic moiety; X is a leaving group; and $X^1$ is an acyloxy group having 1 to 6 carbon atoms.

According to the invention, a 7-methyl-3-methylene-7-octenal acetal compound (1), which is a useful intermediate, can be used as a common intermediate to efficiently produce 7-methyl-3-methylene-7-octenal (2), a 7-methyl-3-methylene-7-octenyl carboxylate compound (4), 3,7-dimethyl-2,7-octadienal (5), a 3,7-dimethyl-2,7-octadienyl carboxylate compound (7), a mixture of a 7-methyl-3-methylene-7-octenyl carboxylate compound (4) and a 3,7-dimethyl-2,7-octadienyl carboxylate compound (7), or a 7-methyl-3-methylene-7-octenal acetal compound (1). In addition, a 3-acyloxymethyl-3-methylene-butenal acetal compound having excellent storage stability can be used to efficiency produce a 7-methyl-3-methylene-7-octenal acetal compound (1). In particular, 7-methyl-3-methylene-7-octenyl propionate, (Z)-3,7-dimethyl-2,7-octadienyl propionate, and (E)-3,7-dimethyl-2,7-octadienyl propionate, which are SJS sex pheromones, can be simultaneously produced.

DETAILED DESCRIPTION OF THE PREFERRED EMBODIMENTS

The chemical formulae of intermediates, reagents, and target compounds in the specification can include stereoisomers such as enantiomers and diastereomers in terms of structure. Each chemical formula is intended to represent all the isomers in each case unless otherwise stated. The isomer may be used alone or as a mixture of two or more isomers.

The inventors have studied the following synthetic strategy. As an example of the 7-methyl-3-methylene-7-octenyl carboxylate compound, a propionate will be described. It is considered that the target compound 7-methyl-3-methylene-7-octenyl propionate (A) can also be produced if 7-methyl-3-methylene-7-octenal (C), which is one of the target compounds in the invention, can be synthesized, because reduction of the aldehyde (C) into 7-methyl-3-methylene-7-octenol (B) and subsequent esterification of the alcohol (B) result in ester (A). It is considered that the 7-methyl-3-methylene-7-octenal (C) can be produced if a corresponding 7-methyl-3-methylene-7-octenal acetal compound (D) can be hydrolyzed in a mild condition without double-bond migration. It is considered that the 7-methyl-3-methylene-7-octenal acetal compound (D) can be synthesized by the coupling reaction of two building blocks each having 5 carbon atoms, in the other words, the coupling reaction between an organometallic reagent (E) as a nucleophilic reagent and an electrophilic reagent having a leaving group X at the allylic position and having 5 carbon atoms (F). On the other hand, it is considered that 3,7-dimethyl-2,7-octadienyl propionate (G), which is one of the target compounds in the invention, can be produced if a corresponding 3,7-dimethyl-2,7-octadienal (I) can be synthesized, because reduction of the aldehyde (I) into 3,7-dimethyl-2,7-octadienol (H) and subsequent esterification of the alcohol (H) results in the ester (G). It is considered that the 3,7-dimethyl-2,7-octadienal (I) can be produced if the exo-double bond at 3-position of 7-methyl-3-methylene-7-octenal (C) can be isomerized into a tri-substituted, conjugated double bond, which is considered to be thermodynamically more stable.

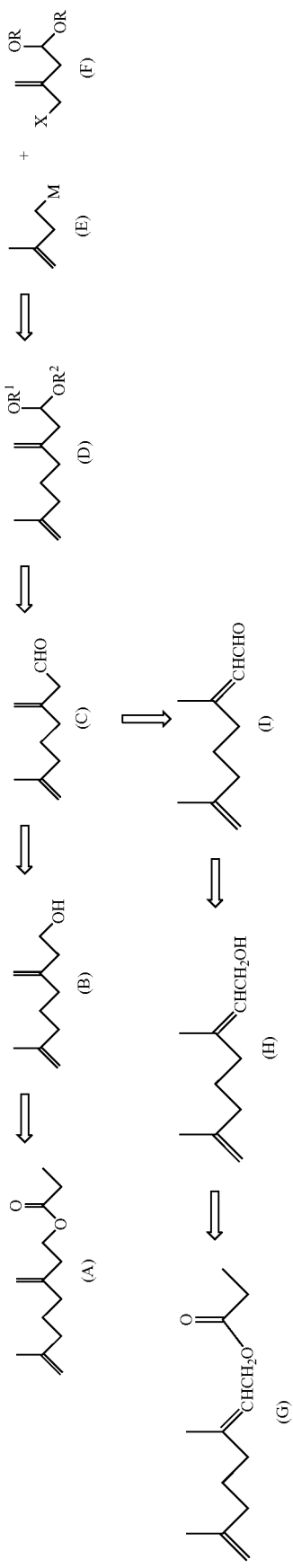

In the scheme, hollow arrows represent transformation in the retrosynthetic analysis, X is a leaving group, and M is a cationic moiety. Chemical Formula (G) means (Z)-3,7-dimethyl-2,7-octadienyl propionate of Formula (Gz), (E)-3,7-dimethyl-2,7-octadienyl propionate of Formula (Ge), or a mixture thereof. Chemical Formula (H) represents (Z)-3,7-dimethyl-2,7-octadienol of Formula (Hz), (E)-3,7-dimethyl-2,7-octadienol of Formula (He), or a mixture thereof. Chemical Formula (I) represents (Z)-3,7-dimethyl-2,7-octadienal of Formula (Iz), (E)-3,7-dimethyl-2,7-octadienal of Formula (Ie), or a mixture thereof.

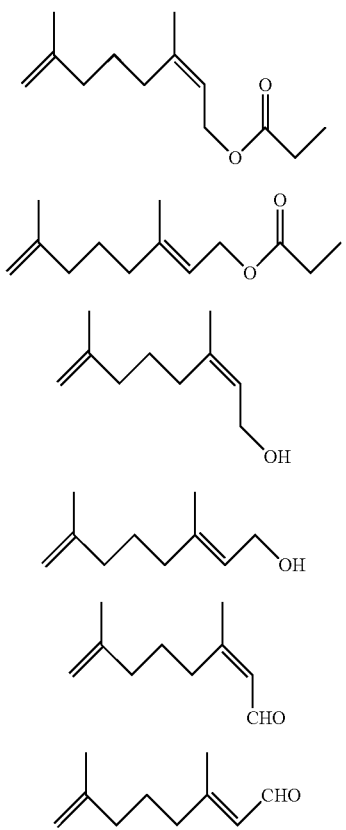

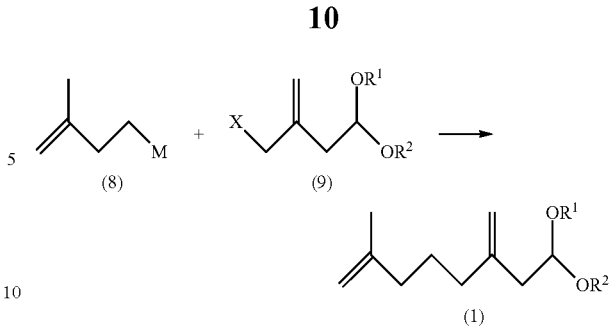

In other words, 7-methyl-3-methylene-7-octenal (C) produced by hydrolysis of a 7-methyl-3-methylene-7-octenal acetal compound (D) can be converted into both 7-methyl-3-methylene-7-octenol (B) and 3,7-dimethyl-2,7-octadienol (H), so that a 7-methyl-3-methylene-7-octenyl carboxylate compound and a 3,7-dimethyl-2,7-octadienyl carboxylate compound can be simultaneously synthesized.

Embodiments of the invention will now be described in detail.

[1] Method for Producing 7-methyl-3-methylene-7-octenal acetal Compound (1)

A 7-methyl-3-methylene-7-octenal acetal compound (1) may be produced by a coupling reaction between a nucleophilic reagent expressed as a 3-methyl-3-butenyl M (8) and an acetal compound (9) having a leaving group X. In the formulae below, M is a cationic moiety, X is a leaving group, and $R^1$ and $R^2$, which may be the same or different, are each an alkyl group having 1 to 6 carbon atoms, or are bonded to each other to form a divalent alkylene group having 2 to 12 carbon atoms.

The nucleophilic reagent 3-methyl-3-butenyl M (8) to be used in the coupling reaction is exemplified by a nucleophilic reagent 3-methyl-3-butenyl M containing a group I or group II metal element of the periodic table or a transition metal element.

Among the nucleophilic reagent 3-methyl-3-butenyl M containing a group I or group II metal element, a 3-methyl-3-butenyl lithium reagent (organolithium reagent) and a 3-methyl-3-butenyl magnesium halide (Grignard reagent) are preferred from the standpoint of reactivity, selectivity, easy preparation and the like.

The nucleophilic reagent 3-methyl-3-butenyl M containing a transition metal element to be used in the coupling reaction may be prepared by a metal exchange reaction of the organolithium reagent or the Grignard reagent with a stoichiometric amount (1 mol) or more of a transition metal compound, or may be formed in the coupling reaction system from the organolithium reagent or the Grignard reagent with a transition metal compound catalyst.

Examples of the transition metal compound to be used in the coupling reaction include transition metal compounds containing copper, iron, nickel, palladium, zinc, silver, or another transition metal. Particularly preferred are copper compounds such as copper(I) chloride, copper(I) bromide, copper(I) iodide, copper(I) cyanide, copper(I) oxide, copper (II) chloride, copper(II) bromide, copper(II) iodide, copper (II) cyanide, copper(II) oxide, and dilithium tetrachlorocuprate ($Li_2CuCl_4$).

The amount of the transition metal compound to be used in the coupling reaction is a catalytic amount (0.0001 to 0.999 mol) to a stoichiometric amount (1 mol) or an excess amount (more than 1 mol and 100 mol or less) relative to 1 mol of the acetal compound (9) having a leaving group X. It is particularly preferably the catalytic amount from the standpoint of economy and safety.

When a transition metal compound is used in the coupling reaction, a phosphorus compound such as a trialkyl phosphite (e.g. triethyl phosphite) and triarylphosphine (e.g. triphenylphosphine) may also be used from the standpoint of enhancement in solubility of the transition metal compound in a solvent.

The cationic moiety M in the nucleophilic reagent 3-methyl-3-butenyl M (8) to be used in the coupling reaction is particularly preferably Li, MgZ, ZnZ, Cu, CuZ, or CuLiZ, wherein Z is a halogen atom or a 3-methyl-3-butenyl group, from the standpoint of easy preparation of the reagent and reactivity. The nucleophilic reagent 3-methyl-3-butenyl M (8) is typically prepared by a conventional method from a 3-methyl-3-butenyl halide, which is a corresponding halide. The halide is preferably a chloride, a bromide, or an iodide.

An acetal compound (9) having a leaving group X, which is the other reactant to be used in the coupling reaction, will be described. Examples of the leaving group X in the acetal compound (9) having the leaving group X include a halogen atom, an acyloxy group, an alkoxy group, an aryloxy group, an alkanesulfonyloxy group, and an arenesulfonyloxy group, which function as a leaving group (anionic moiety) in the coupling reaction. Specifically preferred is a halogen atom or an acyloxy group. The halogen atom is preferably a chlorine atom or a bromine atom, and is particularly preferably a chlorine atom from the standpoint of reactivity and storage stability of the acetal compound (9) having a leaving group X. The acyloxy group is preferably an acyloxy group having 1 to 6 carbon atoms, and is specifically exemplified by unsubstituted or halogen-substituted acyloxy groups such as a formyloxy group, an acetoxy group, a chloroacetyloxy group, a propionyloxy group, a butyryloxy group, a hexanoyloxy group, a dichloroacetyloxy group, a trichloroacetyloxy group and a trifluoroacetyloxy group. The acetoxy group is particularly preferred from the standpoint of reactivity, industrial availability of a raw material, price, and storage stability of the acetal compound (9) having a leaving group X. Examples of the alkoxy group include a methoxy group and an ethoxy group. Examples of the aryloxy group include a phenoxy group. Examples of the alkanesulfonyloxy group include a methanesulfonyloxy group, a trifluoromethanesulfonyloxy group, and a butanesulfonyloxy group. Examples of the arenesulfonyloxy group include a benzenesulfonyloxy group, a p-toluenesulfonyloxy group, and a naphthalenesulfonyloxy group.

In the acetal compound (9) having a leaving group X, $R^1$ and $R^2$, which may be the same or different, are each an alkyl group having 1 to 6 carbon atoms, or are bonded to each other to form a divalent alkylene group having 2 to 12 carbon atoms. Examples of the alkyl group having 1 to 6 carbon atoms include a linear primary alkyl group such as a methyl group, an ethyl group, an n-propyl group, an n-butyl group, an n-pentyl group and an n-hexyl group; a branched primary alkyl group such as an isobutyl group, a 3-methylbutyl group, a neopentyl group and a 4-methylpentyl group; a secondary alkyl group such as an isopropyl group, a sec-butyl group, a 1-methylbutyl group, a 1,2-dimethylpropyl group and a 1-methylpentyl group; and a tertiary alkyl group such as a t-butyl group and a 1,1-dimethylpropyl group. Examples of the divalent alkylene group having 2 to 12 carbon atoms include an ethylene group, a 1,2-propylene group, a 1,3-propylene group, a 1,2-butylene group, a 1,3-butylene group, a 2,3-butylene group, a 1,4-butylene group, and a 2,2-dimethyl-1,3-propylene group. For $R^1$ and $R^2$, the alkyl group having 1 to 6 carbon atoms is preferably a linear primary alkyl group, particularly preferably a methyl group or an ethyl group from the standpoint of easy synthesis or availability of a raw material, price, the reactivity in the hydrolysis described later and the like. The divalent alkylene group having 2 to 10 carbon atoms is preferably an ethylene group, a 1,2-propylene group, a 1,3-propylene group, or a 1,2-butylene group.

The acetal compound (9) having a leaving group X as a reactant in the coupling reaction has the leaving group X at the allylic position, so that the attack site by the nucleophilic reagent 3-methyl-3-butenyl M (8) on the acetal compound (9) having the leaving group X can be either the carbon atom bonded to X or the methylene carbon of the exo-double bond. The $S_N2$ substitution reaction proceeds in the former case, while the $S_N2'$ substitution reaction involving allylic rearrangement proceeds in the latter case. In either case, a 7-methyl-3-methylene-7-octenal acetal compound (1) is produced.

The amounts of the nucleophilic reagent 3-methyl-3-butenyl M (8) and the acetal compound (9) having a leaving group X to be used in the coupling reaction may be selected in consideration of the substrate type, reaction conditions, reaction yield, and economy such as the price of an intermediate. The amount of the nucleophilic reagent 3-methyl-3-butenyl M (8) is preferably 0.02 to 100 mol, more preferably 0.2 to 10 mol, even more preferably 0.5 to 5 mol relative to 1 mol of the acetal compound (9) having a leaving group X.

Examples of the solvent to be used in the coupling reaction preferably include an ether such as diethyl ether, di-n-butyl ether, t-butyl methyl ether, cyclopentyl methyl ether, tetrahydrofuran and 1,4-dioxane. Such an ether may be used together with a hydrocarbon such as hexane, heptane, benzene, toluene, xylene and cumene, or may be used together with an aprotic polar solvent such as N,N-dimethylformamide (DMF), N,N-dimethylacetamide, N,N-dimethylpropionamide, 1,3-dimethyl-2-imidazolidinone (DMI), dimethyl sulfoxide (DMSO) and hexamethylphosphoric triamide (HMPA).

In the coupling reaction step, a lithium salt such as lithium chloride, lithium bromide and lithium iodide may be used as a reaction catalyst in an amount of 0.0001 to 5 mol relative to 1 mol of the acetal compound (9).

The reaction temperature of the coupling reaction is preferably −78° C. to the boiling point of a solvent, more preferably −10° C. to 100° C.

The reaction time of the coupling reaction may be freely selected and is preferably optimized by monitoring the progress of the reaction by means of gas chromatography (GC) or thin-layer chromatography (TLC). Typically, the reaction time is preferably 5 minutes to 240 hours.

When a 7-methyl-3-methylene-7-octenal acetal compound (1) obtained by the above coupling reaction has a sufficient purity, the crude product may be subjected to the next step directly, or may be purified by a method appropriately selected from purification methods commonly used in organic syntheses, such as distillation and various types of chromatography. The distillation is particularly preferred from the standpoint of industrial economy.

Examples of a method for producing a 3-halomethyl-3-butenal acetal compound (9) having a halogen as the leaving group X include a method for producing 3-bromomethyl-3-butenal diethyl acetal (X=Br, $R^1=R^2=C_2H_5$) described in the article by I. V. Mineeva et al., Russian Journal of Organic Chemistry, 45, 1623, (2009). The 3-bromomethyl-3-butenal diethyl acetal may be used as a reactant in the coupling reaction in accordance with the invention. The diethyl acetal is a yellowish liquid immediately after the preparation, but is rapidly discolored to yellow, brown, and then black even when stored with cooling under nitrogen, and the purity markedly deteriorates for a long-time storage. In addition, the diethyl acetal is difficult to purify by an industrial method.

In contrast, a 3-acyloxymethyl-3-butenal acetal compound, which may be prepared by a substitution reaction of replacing the bromine atom of a 3-bromomethyl-3-butenal acetal compound by an acyloxy group, is preferable because it exhibits sufficient reactivity as a reactant in the coupling reaction in accordance with the invention, is relatively stable during a long-term storage, and can be purified by an industrial method such as vacuum distillation. Examples of the 3-acyloxymethyl-3-butenal acetal compound preferably include a compound of General Formula (10). In the formula, $X^1$ is an acyloxy group having 1 to 6 carbon atoms.

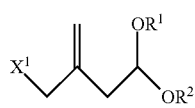

Examples of the substitution reaction of replacing the bromine atom by an acyloxy group include thermally reacting a 3-bromomethyl-3-butenal acetal compound with a carboxylate salt corresponding to a target acyl group in a solvent.

Examples of the carboxylate salt include an alkali metal salt such as a sodium salt, a lithium salt and a potassium salt, and an alkaline earth metal salt such as a magnesium salt and a barium salt.

The amount of the carboxylate salt is preferably 1 to 500 mol, more preferably 1 to 50 mol, even more preferably 1 to 5 mol relative to 1 mol of the 3-bromomethyl-3-butenal acetal compound.

Examples of the solvent for the reaction preferably include water; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; alcohols such as methanol, ethanol, 1-propanol, 2-propanol, ethylene glycol monomethyl ether and diethylene glycol monomethyl ether; nitriles such as acetonitrile; ketones such as acetone and 2-butanone; esters such as ethyl acetate and n-butyl acetate; and aprotic polar solvents such as N,N-dimethylformamide, N,N-dimethylacetamide, dimethyl sulfoxide and hexamethylphosphoric triamide. The solvent may be used singly or in combination of two or more thereof. The aprotic polar solvent or a mixed solvent containing the aprotic polar solvent is particularly preferred from the standpoint of reaction rate and the like.

An appropriate reaction temperature may be selected depending on a carboxylate salt to be used or reaction conditions. It is typically preferably room temperature (i.e. 5 to 35° C., hereinafter the same definition for the room temperature) to the boiling point temperature of a solvent.

An acetal compound having a different leaving group including a 3-alkoxymethyl-3-butenal acetal compound, a 3-aryloxymethyl-3-butenal acetal compound, a 3-alkanesulfonyloxymethyl-3-butenal acetal compound, and a 3-arenesulfonyloxymethyl-3-butenal acetal compound may also be produced by a conventional method.

[2] Method for Producing 7-methyl-3-methylene-7-octenal acetal Compound (1) by Transacetalization A 7-methyl-3-methylene-7-octenal acetal compound (1) having certain substituents as $R^1$ and $R^2$ may be converted through transacetalization into another compound (1) having other substituents as $R^1$ and $R^2$ in consideration of ease in purification due to a change in physical properties such as boiling point, storage stability, the reactivity in the subsequent hydrolysis and the like. The transacetalization will be described in Examples below, and may be carried out, for example, by heating the reactant acetal with an alcohol constituting an intended acetal in an acid catalyst condition. In the acid catalytic transacetalization, it is found that the conversion from a compound (1) having certain substituents as $R^1$ and $R^2$ to another compound (1) having other substituents as $R^1$ and $R^2$ proceeds at a high yield without side reactions such as regioisomerization of a double bond. For these reasons, the transacetalization is favorable as compared with the synthetic method in which a compound (1) having certain substituents as $R^1$ and $R^2$ is hydrolyzed into 7-methyl-3-methylene-7-octenal (2), and then the octenal (2) is subjected to acetalization into another compound (1) having other substituents as $R^1$ and $R^2$.

[3] Method for Producing 7-methyl-3-methylene-7-octenal (2)

Production of 7-methyl-3-methylene-7-octenal (2) by hydrolysis of a 7-methyl-3-methylene-7-octenal acetal compound (1) will next be described.

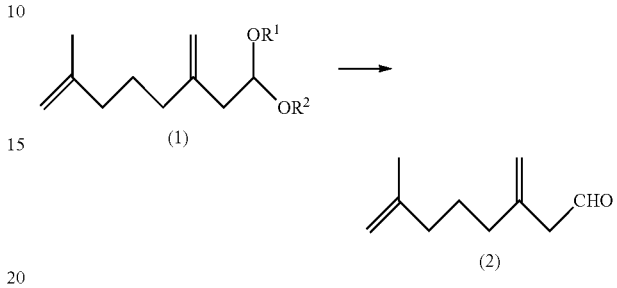

The hydrolysis may be selected from various reactions known as the conversion reaction of an acetal into an aldehyde. The hydrolysis is preferably carried out in the presence of water under an acidic condition from the standpoint of industrial economy. For the reaction, an auxiliary solvent may be used together with the water.

Examples of the acid to be used for the hydrolysis include inorganic acids such as hydrochloric acid, hydrobromic acid, sulfuric acid, nitric acid, phosphoric acid and silica gel; organic acids such as formic acid, acetic acid, propionic acid, oxalic acid, chloroacetic acid, dichloroacetic acid, trichloroacetic acid, trifluoroacetic acid, methanesulfonic acid, benzenesulfonic acid and p-toluenesulfonic acid; and acidic ion exchange resins such as Amberlyst-15. The acid is used singly or in combination of two or more thereof.

Specifically, hydrochloric acid as an inorganic acid, and formic acid, acetic acid, propionic acid and oxalic acid as organic acids are particularly preferable because they are inexpensive and industrially available in large amounts.

The amount of the acid to be used in the hydrolysis depends on $R^1$, $R^2$ and a type of the acid. It is preferably 0.0001 to 1000 mol, more preferably 0.001 to 100 mol relative to 1 mol of the 7-methyl-3-methylene-7-octenal acetal compound (1).

Examples of the auxiliary solvent to be used in the hydrolysis include chlorinated solvents such as methylene chloride, chloroform and trichloroethylene; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran, 1,4-dioxane, ethylene glycol dimethyl ether and diethylene glycol dimethyl ether; alcohols such as methanol, ethanol, 1-propanol, 2-propanol, tert-butyl alcohol, ethylene glycol monomethyl ether and diethylene glycol monomethyl ether; nitriles such as acetonitrile and propionitrile; ketones such as acetone and 2-butanone; esters such as ethyl acetate and n-butyl acetate; and aprotic polar solvents such as N,N-dimethylformamide, N,N-dimethylacetamide, dimethyl sulfoxide and hexamethylphosphoric triamide. The solvent may be used singly or in combination of two or more thereof.

The reaction temperature of the hydrolysis may be appropriately selected depending on a type of the acid or solvent to be used and reaction conditions. Typically, it is preferably −20° C. to a boiling point of the solvent, more preferably −20° C. to room temperature.

The reaction time may be freely selected and is preferably optimized by monitoring the reaction by means of gas chromatography (GC) or thin-layer chromatography (TLC). Typically, the reaction time is preferably 5 minutes to 240 hours.

When 7-methyl-3-methylene-7-octenal (2) is intended to be synthesized selectively (i.e. at yield as high as possible), a mild condition, including use of an acid having low acidity, use of a large amount of a solvent to reduce the substrate concentration in a reaction mixture, a lower reaction temperature and suppression of reaction rate to a degree for easy control, is selected from the above hydrolysis conditions to prevent isomerization of a double bond.

On the contrary, along with the synthesis of 7-methyl-3-methylene-7-octenal (2), the compound (2) may be allowed to undergo conversion involving the regioisomerization of a double bond into 3,7-dimethyl-2,7-octadienal (5). As a result, a mixture of compounds (2) and (5) may be intentionally and simultaneously synthesized.

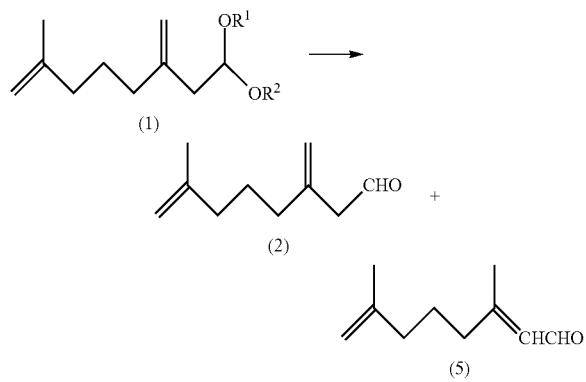

In the simultaneous productions, the production ratio of the compound (2) to the compound (5), and the production ratio of (5z) and (5e), which are geometric isomers of the compound (5), may be considered. This point will be described later.

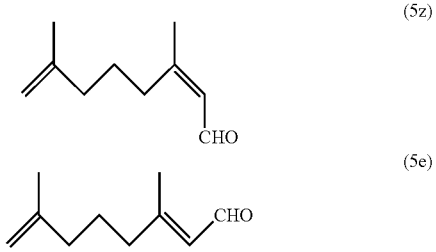

It is also preferable to monitor the progresses of the hydrolysis and the isomerization by means of gas chromatography (GC) or thin-layer chromatography (TLC) to stop the reaction at an intended ratio. However, when 3,7-dimethyl-2,7-octadienal (5) is intended to be selectively produced, a method of isomerizing 7-methyl-3-methylene-7-octenal (2) into 3,7-dimethyl-2,7-octadienal (5) in a basic condition is better than the hydrolysis in an acidic condition to completely obtain 3,7-dimethyl-2,7-octadienal (5), as described later.

When the 7-methyl-3-methylene-7-octenal (2) produced by the above hydrolysis has a sufficient purity, the crude product may be subjected to the next step directly, or may be purified by a method appropriately selected from purification methods commonly used in organic syntheses, such as distillation and various types of chromatography. The distillation is particularly preferable from the standpoint of industrial economy.

[4] Method for Producing 7-methyl-3-methylene-7-octenol (3)

The formyl group of the 7-methyl-3-methylene-7-octenal (2) produced above is reduced to obtain a corresponding 7-methyl-3-methylene-7-octenol (3).

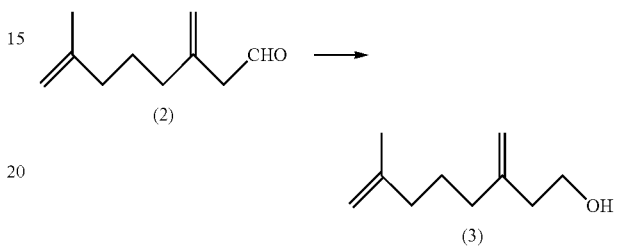

The reduction may be selected from known reduction reactions from an aldehyde to an alcohol. In a typical reduction, a reactant in a solvent is reacted with a reducing agent, while being optionally cooled or heated.

Examples of the reducing agent to be used for the reduction include hydrogen; boron compounds such as borane, alkylboranes, dialkylboranes and bis(3-methyl-2-butyl)borane; dialkylsilanes; trialkylsilanes; alkylaluminums; dialkylaluminums; metal hydrides such as sodium hydride, lithium hydride, potassium hydride and calcium hydride; and complex hydrides and alkoxy or alkyl derivatives thereof such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-tert-butoxyaluminum hydride, sodium bis(2-methoxyethoxy) aluminum hydride, lithium triethylborohydride and diisobutylaluminum hydride. The complex hydrides are preferable from the standpoint of reaction conditions, easy work-up, easy isolation of a product and the like.

The amount of the reducing agent to be used in the reduction varies depending on a type of the reducing agent, reaction conditions and the like. Typically, it is preferably 0.5 mol to an excess amount (i.e. more than 1 mol and 1,000,000 mol or less), more preferably 0.9 to 200 mol relative to 1 mol of a substrate.

Examples of the solvent to be used in the reduction preferably include water; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; alcohols such as methanol, ethanol, 1-propanol, 2-propanol, ethylene glycol monomethyl ether and diethylene glycol monomethyl ether; nitriles such as acetonitrile; ketones such as acetone and 2-butanone; esters such as ethyl acetate and n-butyl acetate; and aprotic polar solvents such as N,N-dimethylformamide, dimethyl sulfoxide and hexamethylphosphoric triamide. The solvent may be used singly or in combination of two or more thereof.

The solvent to be used in the reduction is appropriately selected depending on a type of the reducing agent. Examples of the preferable combination of the reducing agent and the solvent include the combination of sodium borohydride as the reducing agent and a solvent selected from the group consisting of water, an alcohol, an ether, a mixed solvent of an ether and an alcohol, and a mixed solvent of an ether and a hydrocarbon; and the combination of lithium aluminum hydride as the reducing agent and a solvent selected from the group consisting of an ether, and a mixed solvent of an ether and a hydrocarbon.

The reaction temperature of the reduction varies depending on a type of the reducing reagent or the solvent to be used. For example, when lithium aluminum hydride in tetrahydrofuran is used as the reducing agent, the reaction temperature is preferably −78 to 50° C., more preferably −70 to 20° C.

The reaction time of the reduction may be freely selected. The reaction is preferably completed by monitoring the reaction by means of gas chromatography (GC) or silica gel thin-layer chromatography (TLC) from the standpoint of yield. Typically, the reaction time is preferably 5 to 240 hours.

The reducing agent or the reaction condition is preferably selected so as not to reduce the double bonds of the reactants (2) and/or (5). Particularly in the reduction of 3,7-dimethyl-2,7-octadienal (5) to 3,7-dimethyl-2,7-octadienol (6), it is preferable to select the reducing agent or reaction condition to enhance the production of 3,7-dimethyl-2,7-octadienol (6) as a target product by 1,2-reduction, while suppressing the production of 3,7-dimethyl-7-octenol as a by-product by 1,4-reduction.

When the 7-methyl-3-methylene-7-octenol (3) produced by the reduction has a sufficient purity or a sufficient isomer ratio, the crude product may be subjected to the next step directly, or may be subjected to purification or isomer separation by a method appropriately selected from purification methods and isomer separation methods commonly used in organic syntheses, such as distillation and various types of chromatography. The distillation is particularly preferable from the standpoint of industrial economy.

[5] Method for Producing 7-methyl-3-methylene-7-octenyl carboxylate Compound (4)

The 7-methyl-3-methylene-7-octenol (3) produced above may be esterified to obtain a corresponding 7-methyl-3-methylene-7-octenyl carboxylate compound (4).

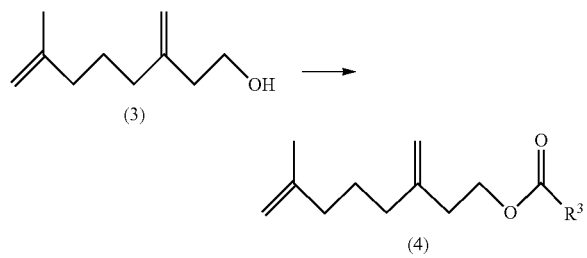

$R^3$ is a hydrogen atom or a monovalent hydrocarbon group having 1 to 6 carbon atoms. Examples of the monovalent hydrocarbon group having 1 to 6 carbon atoms include a linear, branched or cyclic, saturated or unsaturated alkyl group, alkenyl group or aryl groups, and preferably include a methyl group, an ethyl group, an n-propyl group, an n-butyl group, an n-pentyl group, an n-hexyl group, an isopropyl group, an isobutyl group, an isopentyl group, an isohexyl group, a sec-butyl group, a tert-butyl group, a vinyl group, an isopentenyl group, a propenyl group, an allyl group, a 1-methyl-1-propenyl group, a 2-methyl-1-propenyl group, and a phenyl group.

The esterification may be selected from known ester production methods including a reaction with an acylating agent, a reaction with a carboxylic acid, a transesterification, and a method in which 7-methyl-3-methylene-7-octenol (3) is converted into an alkylating agent and then the alkylating agent is reacted with a carboxylic acid.

In the reaction with an acylating agent, 7-methyl-3-methylene-7-octenol (3) as a reactant is reacted, in a single solvent or a mixture of two or more solvents, with an acylating agent and a base sequentially or simultaneously.

Examples of the acylating agent in the reaction with the acylating agent preferably include an acyl chloride, an acyl bromide, a carboxylic anhydride, a carboxylic trifluoroacetic anhydride, a carboxylic methanesulfonic anhydride, a carboxylic trifluoromethanesulfonic anhydride, a carboxylic benzenesulfonic anhydride, a carboxylic p-toluenesulfonic anhydride, and p-nitrophenyl carboxylate compound.

Examples of the base to be used in the reaction with an acylating agent preferably include triethylamine, diisopropylethylamine, N,N-dimethylaniline, N,N-diethylaniline, pyridine, and 4-dimethylaminopyridine.

The solvent to be used in the reaction with an acylating agent may be the above base, or may be a single solvent or mixed solvent of two or more solvents selected from chlorinated solvents such as methylene chloride, chloroform and trichloroethylene; hydrocarbons such as hexane, heptane, benzene, toluene, xylene and cumene; ethers such as diethyl ether, dibutyl ether, t-butyl methyl ether, diethylene glycol diethyl ether, diethylene glycol dimethyl ether, tetrahydrofuran and 1,4-dioxane; nitriles such as acetonitrile; ketones such as acetone and 2-butanone; esters such as ethyl acetate and n-butyl acetate; and aprotic polar solvents such as N,N-dimethylformamide, dimethylsulfoxide and hexamethylphosphoric triamide. The reaction using an acylating agent such as a carboxylic anhydride may be carried out with an acid catalyst instead of the base.

The amount of the acylating agent is preferably 1 to 500 mol, more preferably 1 to 50 mol, even more preferably 1 to 5 mol relative to 1 mol of 7-methyl-3-methylene-7-octenol (3).

The acid catalyst to be used instead of the base in the reaction with an acylating agent is preferably selected from inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

The reaction temperature of the reaction with an acylating agent may be appropriately selected depending on a type of an acylating agent to be used and reaction conditions. Typically, it is preferably −50° C. to the boiling point of the solvent, more preferably −20° C. to room temperature.

The reaction with a carboxylic acid is a dehydration reaction between 7-methyl-3-methylene-7-octenol (3) and the carboxylic acid, and is typically carried out with an acid catalyst.

The amount of the carboxylic acid is preferably 1 to 500 mol, more preferably 1 to 50 mol, even more preferably 1 to 5 mol relative to 1 mol of the reactant 7-methyl-3-methylene-7-octenol (3).

Examples of the acid catalyst to be used in the reaction of 7-methyl-3-methylene-7-octenol (3) with a carboxylic acid include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. The acid is used singly or in combination of two or more thereof.

The amount of the acid catalyst to be used in the reaction with a carboxylic acid is preferably 0.0001 to 100 mol, more preferably 0.001 to 1 mol, even more preferably a catalytic amount of 0.01 to 0.05 mol relative to 1 mol of 7-methyl-3-methylene-7-octenol (3).

Examples of the solvent to be used in the reaction of 7-methyl-3-methylene-7-octenol (3) with a carboxylic acid include the same examples as those of the solvent to be used in the reaction with an acylating agent.

The reaction temperature of the reaction with a carboxylic acid may be appropriately selected depending on reaction conditions. Typically, it is preferably −50° C. to the boiling point of the solvent, more preferably room temperature to the boiling point of the solvent. A solvent containing a hydrocarbon such as hexane, heptane, benzene, toluene, xylene and cumene may be used to proceed the reaction, while generated water is removed from the system by azeotropy. In this case, the water may be distilled off while the reaction mixture is refluxed at the boiling point of the solvent at normal pressure. Alternatively, the water may be distilled off at a temperature lower than the boiling point under reduced pressure.

The transesterification is carried out by reacting 7-methyl-3-methylene-7-octenol (3) with an alkyl carboxylate in the presence of a catalyst, while removing the generated alcohol. The alkyl carboxylate is preferably a primary alkyl ester of a carboxylic acid and is particularly preferably a methyl carboxylate, an ethyl carboxylate, and an n-propyl carboxylate from the standpoint of price, easy progress of the reaction and the like.

The amount of the alkyl carboxylate to be used in the transesterification is preferably 1 to 500 mol, more preferably 1 to 50 mol, even more preferably 1 to 5 mol relative to 1 mol of the reactant 7-methyl-3-methylene-7-octenol (3).

Examples of the catalyst to be used in the transesterification include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; bases such as sodium methoxide, sodium ethoxide, potassium t-butoxide and 4-dimethylaminopyridine; salts such as sodium cyanide, potassium cyanide, sodium acetate, potassium acetate, calcium acetate, tin acetate, aluminum acetate, aluminum acetoacetate and alumina; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. The catalyst are used singly or in combination of two or more thereof.

The amount of the catalyst to be used in the transesterification is preferably 0.0001 to 100 mol, more preferably 0.001 to 1 mol, even more preferably a catalytic amount of 0.01 to 0.05 mol relative to 1 mol of 7-methyl-3-methylene-7-octenol (3).

The transesterification may be carried out without a solvent (an alkyl carboxylate as the reaction reagent may be used also as the solvent). Such a reaction is preferable from the standpoint of omission of necessary additional operations such as concentration and solvent recovery. A solvent may be used auxiliarily.

Examples of the solvent to be used in the transesterification preferably include hydrocarbons such as hexane, heptane, benzene, toluene, xylene and cumene; and ethers such as diethyl ether, dibutyl ether, diethylene glycol diethyl ether, diethylene glycol dimethyl ether, tetrahydrofuran and 1,4-dioxane. The solvent is used singly or in combination of two or more thereof.

The reaction temperature of the transesterification may be appropriately selected depending on a type of the alkyl carboxylate to be used and reaction conditions. The transesterification is typically carried out with heating. The reaction is carried out around the boiling point of a lower alcohol which will be generated during the transesterification. The lower alcohol is an alcohol having 1 to 3 carbon atoms and has a low boiling point, and examples thereof include methanol, ethanol and 1-propanol. The reaction is carried out, while the generated lower alcohol is distilled off, to obtain good results. The alcohol may be distilled off at a temperature lower than the boiling point under reduced pressure.

In the method in which 7-methyl-3-methylene-7-octenol (3) is converted into an alkylating agent and then the alkylating agent is reacted with a carboxylic acid, 7-methyl-3-methylene-7-octenol (3) is converted, for example, into a corresponding halide such as chloride, bromide and iodide, or a corresponding sulfonate such as methanesulfonate, trifluoromethanesulfonate, benzenesulfonate and p-toluenesulfonate, and is then reacted with a carboxylic acid typically in a solvent in a basic condition. The solvent, base, reaction temperature and reaction time are, for example, the same as those of the reaction of 7-methyl-3-methylene-7-octenol (3) with an acylating agent. Instead of a combination of the carboxylic acid and the base, a carboxylate salt such as a sodium carboxylate, a lithium carboxylate, a potassium carboxylate and an ammonium carboxylate may be used.

The 7-methyl-3-methylene-7-octenyl carboxylate compound (4) produced in the above esterification may be subjected to purification or isomer separation by a method appropriately selected from purification methods or isomer separation methods commonly used in organic syntheses, such as distillation and various types of chromatography. The distillation is particularly preferable from the standpoint of industrial economy.

[6] Method for Producing 3,7-dimethyl-2,7-octadienal (5) and Method for Simultaneously Producing 7-methyl-3-methylene-7-octenal (2) and 3,7-dimethyl-2,7-octadienal (5)

7-Methyl-3-methylene-7-octenal (2) may be subjected to regioisomerization of a double bond to obtain 3,7-dimethyl-2,7-octadienal (5).

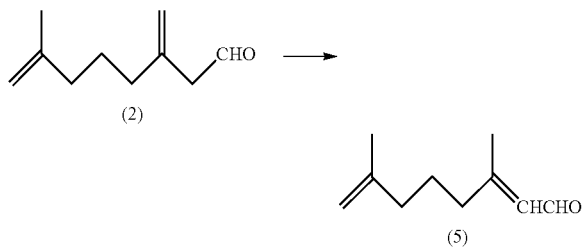

The isomerization proceeds in various conditions including an acidic condition and a basic condition.

Examples of the acid to be used in the isomerization in the presence of the acid include those described in the hydrolysis of the 7-methyl-3-methylene-7-octenal acetal compound (1); and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. An acid selected from these examples may be used in the isomerization from 7-methyl-3-methylene-7-octenal (2) to 3,7-dimethyl-2,7-octadienal (5). For the isomerization, the production ratio of (5z) and (5e), which are geometric isomers of 3,7-dimethyl-2,7-octadienal (5), may be considered.

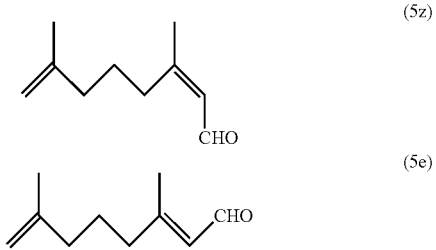

The isomerization may also be allowed to proceed, while keeping the reaction conditions for hydrolysis of the 7-methyl-3-methylene-7-octenal acetal compound (1). However, severe conditions during the acidic isomerization, such as an extremely high acidic condition and a high temperature condition, should be avoided because such sever conditions may lead to acid-catalyzed cyclization to generate a by-product such as 2-(1,3-dimethyl-2-cyclohexenyl)ethanal.

In the isomerization in the presence of a base, 7-methyl-3-methylene-7-octenal (2) is reacted with a base without solvent or in a solvent. The reaction is considered to proceed through deprotonation and reprotonation at the α-position of the aldehyde, and the base capable of converting the aldehyde into an enol may be used.

Examples of the base to be used in the isomerization in the presence of the base include ammonia; hydroxylamine; hydroxides such as lithium hydroxide, sodium hydroxide, potassium hydroxide and tetra-n-butylammonium hydroxide; hydrides such as lithium hydride, sodium hydride and potassium hydride; alkoxides such as lithium methoxide, lithium ethoxide, sodium methoxide, sodium ethoxide and potassium t-butoxide; metal amides such as lithium amide, sodium amide, lithium diisopropylamide, lithium bis-trimethylsilylamide, lithium tetramethylpiperidide and lithium isopropylcyclohexylamide; organic amines such as ethylamine, diethylamine, triethylamine, diisopropylamine, diisopropylethylamine, ethylenediamine, N,N,N',N'-tetramethylethylenediamine, diazabicyclo[4.3.0]-5-nonene (DBN), diazabicyclo[2.2.2]octane, 1,8-diazabicyclo[5.4.0]-7-undecene, aniline, N-methylaniline, N,N-dimethylaniline, N,N-diethylaniline, 1-naphthylamine, 2-naphthylamine, pyridine, 4-dimethylaminopyridine, triazine, pyrrolidine, piperidine, piperazine, morpholine and imidazole; and organometallic compounds such as triphenylmethyllithium, triphenylmethylsodium, triphenylmethylpotassium, methyllithium, phenyllithium, n-butyllithium, s-butyllithium, t-butyllithium and ethyl magnesium halides. The base is used singly or in combination of two or more thereof. The organic amines are preferable from the standpoint of easy reaction, a required amount, easy work-up and the like.

The amount of the base to be used in the isomerization in the presence of the base may be a catalytic amount (0.0001 to 0.999999 mol) to a stoichiometric amount (1 mol), or an excess amount (more than 1 and 1,000,000 mol or less) relative to 1 mol of the reactant 7-methyl-3-methylene-7-octenal (2). It is preferably the catalytic amount to 200 mol relative to 1 mol of the reactant 7-methyl-3-methylene-7-octenal (2).

The solvent to be used in the isomerization in the presence of the base may be the above base which will be used as it is, or may be a single solvent or mixed solvent of two or more solvents selected from water; alcohols such as methanol, ethanol and n-propanol; chlorinated solvents such as methylene chloride, chloroform and trichloroethylene; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; nitriles such as acetonitrile; ketones such as acetone and 2-butanone; esters such as ethyl acetate and n-butyl acetate; and aprotic polar solvents such as N,N-dimethylformamide, dimethylsulfoxide and hexamethylphosphoric triamide.

The reaction temperature of the isomerization may be appropriately selected depending on a type of the base to be used and reaction conditions. Typically, it is preferably −50° C. to the boiling point of the solvent, more preferably −20° C. to room temperature. The geometric isomer ratio of target compounds (5), in other words, the ratio of (5z) to (5e) varies depending on a type or amount of the base to be used and reaction conditions, so that an appropriate reagent and conditions may be selected in consideration of the geometric isomer ratio.

The reaction time of the isomerization may be freely selected. The conversion and the isomer ratio may be optimized by monitoring the reaction by means of gas chromatography (GC) or thin-layer chromatography (TLC). Typically, the reaction time is preferably 5 minutes to 240 hours.

When the 3,7-dimethyl-2,7-octadienal (5) or the mixture of 7-methyl-3-methylene-7-octenal (2) and 3,7-dimethyl-2,7-octadienal (5) produced by the above isomerization has a sufficient purity or a intended isomer ratio, the crude product may be subjected to the next step directly, or may be subjected to purification or isomer separation by a method appropriately selected from purification methods and isomer separation methods commonly used in organic syntheses, such as distillation and various types of chromatography. The distillation is particularly preferable from the standpoint of industrial economy.

[7] Method for Producing 3,7-dimethyl-2,7-octadienol (6)

The formyl group of the 3,7-dimethyl-2,7-octadienal (5) produce above may be reduced to obtain a corresponding 3,7-dimethyl-2,7-octadienol (6).

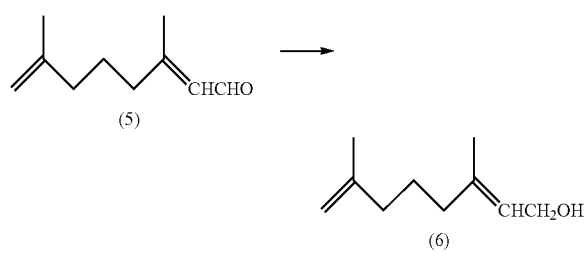

The reduction conditions are the same as those for the method for producing 7-methyl-3-methylene-7-octenol (3).

The reducing agent or the reaction conditions are preferably selected so as to avoid reduction of the double bonds of 3,7-dimethyl-2,7-octadienal (5). In the reduction of 3,7-dimethyl-2,7-octadienal (5) to 3,7-dimethyl-2,7-octadienol (6), it is preferable to select such a reducing agent or reaction conditions as to produce a target compound 3,7-dimethyl-2,7-octadienol (6) by 1,2-reduction, while suppressing an amount of the by-product 3,7-dimethyl-7-octenol by 1,4-reduction.

When the 3,7-dimethyl-2,7-octadienol (6) produced by the above reduction has a sufficient purity or an intended isomer ratio, the crude product may be subjected to the next step directly, or may be subjected to purification or isomer separation by a method appropriately selected from purification methods and isomer separation methods commonly used in organic syntheses, such as distillation and various types of chromatography. The distillation is particularly preferable from the standpoint of industrial economy.

[8] Method for Producing 3,7-dimethyl-2,7-octadienyl carboxylate Compound (7)

The alcohol compound 3,7-dimethyl-2,7-octadienol (6) produced above is esterified to obtain a corresponding 3,7-dimethyl-2,7-octadienyl carboxylate compound (7).

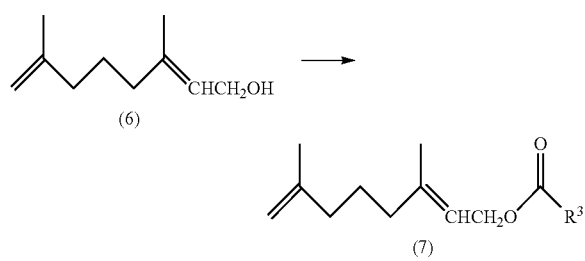

R³ is a hydrogen atom or a monovalent hydrocarbon group having 1 to 6 carbon atoms. Examples of the monovalent hydrocarbon group having 1 to 6 carbon atoms include those described in the method for producing a 7-methyl-3-methylene-7-octenyl carboxylate compound (4).

The esterification conditions are the same as those described in the method for producing a 7-methyl-3-methylene-7-octenyl carboxylate compound (4).

The 3,7-dimethyl-2,7-octadienyl carboxylate compound (7) produced above may be purified by a method appropriately selected from purification methods commonly used in organic syntheses, such as distillation under reduced pressure and various types of chromatography. The distillation under reduced pressure is preferable from the standpoint of industrial economy.

[9] Method for Simultaneously Producing 7-methyl-3-methylene-7-octenol (3) and 3,7-dimethyl-2,7-octadienol (6)

The formyl groups of the mixture of 7-methyl-3-methylene-7-octenal (2) and 3,7-dimethyl-2,7-octadienal (5) produced above may be reduced to obtain a corresponding mixture of 7-methyl-3-methylene-7-octenol (3) and 3,7-dimethyl-2,7-octadienol (6).

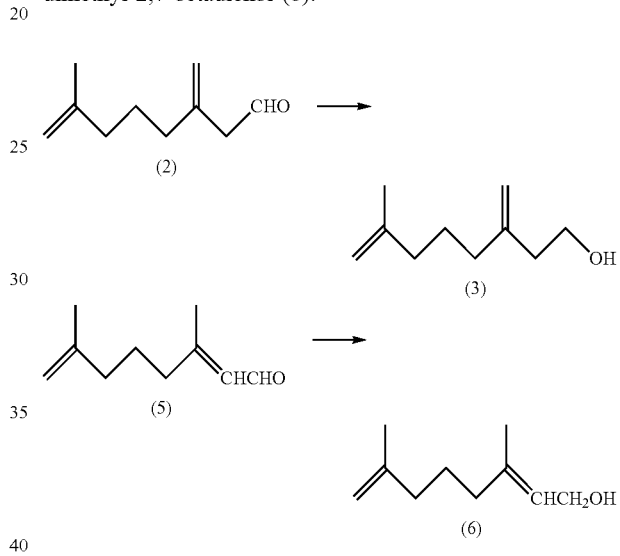

The reduction conditions are the same as those for the method for producing 7-methyl-3-methylene-7-octenol (3).

The reducing agent or the reaction conditions are preferably selected so as to avoid reduction of the double bonds of 3,7-dimethyl-2,7-octadienal (5). For the reduction of 3,7-dimethyl-2,7-octadienal (5) to 3,7-dimethyl-2,7-octadienol (6), it is preferable to select such a reducing agent or reaction conditions as to produce a target compound 3,7-dimethyl-2,7-octadienol (6) by 1,2-reduction, while suppressing an amount of the by-product 3,7-dimethyl-7-octenol by 1,4-reduction.

When a mixture of 7-methyl-3-methylene-7-octenol (3) and 3,7-dimethyl-2,7-octadienol (6) produced by the above reduction has a sufficient purity or an intended isomer ratio, the crude product may be subjected to the next step directly, or may be subjected to purification or isomer separation by a method appropriately selected from purification methods and isomer separation methods commonly used in the organic syntheses, such as distillation and various types of chromatography. The distillation is particularly preferable from the standpoint of industrial economy.

[10] Method for Simultaneously Producing 7-methyl-3-methylene-7-octenyl carboxylate Compound (4) and 3,7-dimethyl-2,7-octadienyl carboxylate Compound (7)

The mixture of 7-methyl-3-methylene-7-octenol (3) and 3,7-dimethyl-2,7-octadienol (6) produced above may be esterified to obtain a corresponding mixture of a 7-methyl-3-methylene-7-octenyl carboxylate compound (4) and a 3,7-dimethyl-2,7-octadienyl carboxylate compound (7).

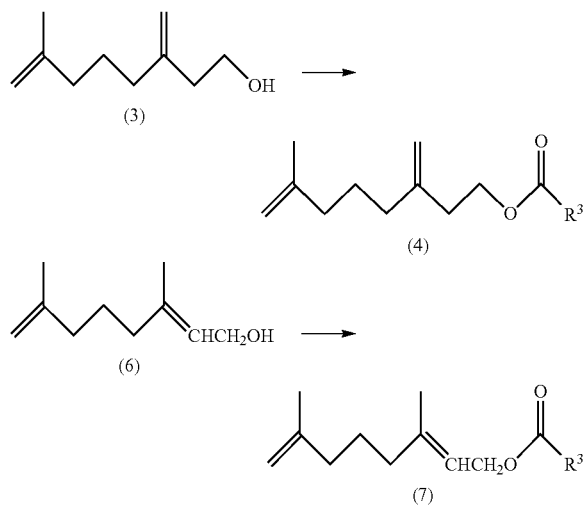

R³ is a hydrogen atom or a monovalent hydrocarbon group having 1 to 6 carbon atoms. Examples of the monovalent hydrocarbon group having 1 to 6 carbon atoms include those described in the method for producing a 7-methyl-3-methylene-7-octenyl carboxylate compound (4).

The esterification conditions are the same as those described in the method for producing a 7-methyl-3-methylene-7-octenyl carboxylate compound (4).

The mixture of a 7-methyl-3-methylene-7-octenyl carboxylate compound (4) and a 3,7-dimethyl-2,7-octadienyl carboxylate compound (7) produced by the above esterification may be subjected to purification or isomer separation by a method appropriately selected from purification methods and isomer separation methods commonly used in organic syntheses, such as distillation and various types of chromatography. The distillation is particularly preferable from the standpoint of industrial economy.

As described above, the 7-methyl-3-methylene-7-octenal acetal compound may be used as a common intermediate to efficiently produce the 7-methyl-3-methylene-7-octenal, the 7-methyl-3-methylene-7-octenyl carboxylate compound, the 3,7-dimethyl-2,7-octadienal, the 3,7-dimethyl-2,7-octadienyl carboxylate compound, and the mixture of the 7-methyl-3-methylene-7-octenyl carboxylate compound and the 3,7-dimethyl-2,7-octadienyl carboxylate compound.

EXAMPLES

The invention will next be described in further detail with reference to Examples. It should not be construed that the invention is limited to or by Examples.

The purities of raw materials, products and intermediates are determined by gas chromatographic (GC) analyses and are expressed with % GC. The isomer ratio of products or intermediates is expressed as an area ratio by GC analysis.
GC Conditions
  GC: Shimazdu GC-14A,
  Column: 5% Ph-Me silicone, 0.25 mmϕ×25 m, Carrier gas: He, and
  Detector: FID.

The yield is the conversion yield based on % GC. Materials to be used in a reaction and products produced by the reaction are not always 100% pure, so that the conversion yield (%) is calculated in accordance with 100×[{(weight of product obtained by reaction)×(% GC)}/(molecular weight of product)]/[{(weight of starting material in reaction)×(% GC)}/(molecular weight of starting material)]. The detection sensitivity of gas chromatography varies with compounds, so that the conversion yield may exceed 100% especially when a material or a product is crude.

A compound sample for spectrum measurement was prepared by optional purification of a crude product.

Example 1: Production of 3-acetoxymethyl-3-butenal diethyl acetal [R¹=R²=CH₂CH₃=Et, X¹=OCOCH₃=OAc in General Formula (10)]

Under a nitrogen atmosphere, a mixture of 94.0 g of 3-bromomethyl-3-butenal diethyl acetal, 100 g of sodium acetate and 1,000 ml of N,N-dimethylacetamide was stirred at 100 to 120° C. for 2 hours. After cooled, the reaction mixture was poured in a saturated aqueous sodium hydrogen carbonate solution and extracted with n-hexane.

The organic phase was subjected to common work-up of washing, drying and concentration to obtain 63.6 g of crude 3-acetoxymethyl-3-butenal diethyl acetal (1) (63.4% GC, yield: 47%). A part of the crude product was distilled under reduced pressure to obtain a sample (86.5% GC) for spectrum measurement.
3-Acetoxymethyl-3-butenal diethyl acetal
  Colorless oil.
  Boiling point: 69° C./399 Pa.
  IR (D-ATR): ν=2976, 2931, 2879, 1743, 1652, 1444, 1373, 1230, 1126, 1058 cm⁻¹.
  ¹H-NMR (500 MHz, CDCl₃): δ=1.18 (6H, t, J=7.1 Hz), 2.07 (3H, s), 2.38 (2H, d, J=5.7 Hz), 3.45-3.52 (2H, m), 3.60-3.68 (2H, m), 4.55 (2H, s), 4.58 (1H, t, J=5.7 Hz), 5.04 (1H, br. s), 5.10 (1H, br. s) ppm.
  ¹³C-NMR (125 MHz, CDCl₃): δ=15.19 (2C), 20.87, 37.81, 61.41 (2C), 67.04, 102.02, 114.84, 139.65, 170.58 ppm.
  GC-MS (EI, 70 eV): 29, 47, 61, 75, 103 (base peak), 127, 171, 215 [(M−H)⁺].

Example 2: Production of 3-acetoxymethyl-3-butenal dibutyl acetal [R¹=R²=CH₂CH₂CH₂CH₃=Bu, X¹=OCOCH₃=OAc in General Formula (10)]

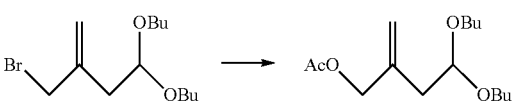

In the same manner as in Example 1 except that 9.10 g of 3-bromomethyl-3-butenal dibutyl acetal (82.0% GC) was used in place of 3-bromomethyl-3-butenal diethyl acetal, 4.85 g of crude 3-acetoxymethyl-3-butenal dibutyl acetal (70.0% GC, yield: 70%) was produced. A part of the crude product was purified by silica gel column chromatography to obtain a sample (90.5% GC) for spectrum measurement.

3-Acetoxymethyl-3-butenal dibutyl acetal

Colorless oil.

IR (D-ATR): v=2959, 2934, 2873, 1745, 1653, 1460, 1374, 1229, 1116, 1071, 1046 cm$^{-1}$.

$^1$H-NMR (500 MHz, CDCl$_3$): δ=0.90 (6H, t, J=7.3 Hz), 1.32-1.40 (2H, m), 1.50-1.57 (2H, m), 2.07 (3H, s), 2.38 (2H, d, J=5.8 Hz), 3.39-3.44 (2H, m), 3.56-3.60 (2H, m), 4.55 (2H, s), 4.56 (1H, t, J=5.8 Hz), 5.03 (1H, br. s), 5.10 (1H, br. s) ppm.

$^{13}$C-NMR (125 MHz, CDCl$_3$): δ=13.83 (2C), 19.36 (2C), 20.88, 31.86 (2C), 37.70, 65.70 (2C), 67.09, 102.24, 114.80, 139.71, 170.58 ppm.

GC-MS (EI, 70 eV): 43, 57 (base peak), 83, 103, 159, 199, 271 [(M−H)$^+$].

Example 3: Production No. 1 of 7-methyl-3-methylene-7-octenal diethyl acetal
[R$^1$=R$^2$=CH$_2$CH$_3$=Et in General Formula (1)]

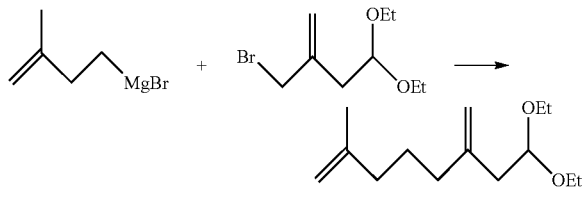

Under a nitrogen atmosphere, a mixture of 32.1 g of 3-bromomethyl-3-butenal diethyl acetal which had been produced from ethyl 3,3-diethoxypropionate as a starting material in accordance with a method described in I. V. Mineeva et al., Russian Journal of Organic Chemistry, 45, 1623 (2009), 30 mg of copper(I) iodide, 45 mg of triethylphosphite and 200 ml of tetrahydrofuran was stirred on ice. The mixture was subjected to dropwise addition, at 15° C. or less over 40 minutes, of 250 ml of a 0.75M 3-methyl-3-butenyl magnesium bromide solution in tetrahydrofuran which had been produced as the Grignard reagent from 3-methyl-3-butenyl bromide, 3.10 g of 1,2-dibromoethane, 4.44 g of magnesium and 220 ml of tetrahydrofuran by a common method. The reaction mixture was stirred on ice for 100 minutes. Then the mixture was subjected to addition of a saturated aqueous ammonium chloride solution, and extracted with ethyl acetate. The separated organic phase was subjected to common work-up of washing, drying and concentration to obtain a crude product. The crude product was distilled under reduced pressure to obtain 18.38 g of 7-methyl-3-methylene-7-octenal diethyl acetal (93% GC, yield: 74%).

7-Methyl-3-methylene-7-octenal diethyl acetal

Colorless oil.

Boiling point: 71-74° C./266 Pa.

IR (D-ATR): v=3074, 2975, 2932, 1648, 1444, 1372, 1128, 1061, 1023, 888 cm$^{-1}$.

$^1$H-NMR (500 MHz, CDCl$_3$): δ=1.19 (6H, t, J=7 Hz), 1.54-1.60 (2H, m), 1.70 (3H, s), 2.00 (2H, t, J=7.6 Hz), 2.05 (2H, t, J=7.6 Hz), 2.34 (2H, d, J=5.7 Hz), 3.46-3.54 (2H, m), 3.61-3.68 (2H, m), 4.61 (1H, t, J=5.7 Hz), 4.66 (1H, br. s), 4.69 (1H, br. s), 4.82-4.83 (2H, m) ppm.

$^{13}$C-NMR (125 MHz, CDCl$_3$): δ=15.24 (2C), 22.35, 25.52, 36.09, 37.37, 40.19, 61.00 (2C), 102.07, 109.86, 111.68, 145.20, 145.77 ppm.

GC-MS (EI, 70 eV): 29, 47, 75, 103 (base peak), 119, 135, 225 [(M−H)$^+$].

Example 4: Production No. 2 of 7-methyl-3-methylene-7-octenal diethyl acetal
[R$^1$=R$^2$=CH$_2$CH$_3$=Et in General Formula (1)]

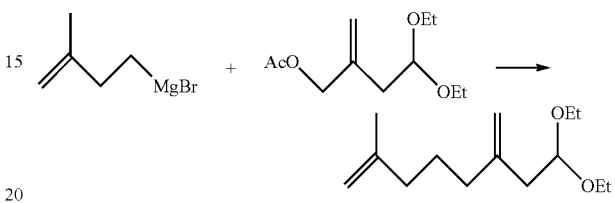

In the same manner as in Example 3 except that 10.0 g of 3-acetoxymethyl-3-butenal diethyl acetal (86.5% GC) was used in place of 3-bromomethyl-3-butenal diethyl acetal, 12.37 g of 7-methyl-3-methylene-7-octenal diethyl acetal (80.8% GC, quantitative yield) was produced. The obtained target compound was identical with the target compound in Example 3.

Example 5: Production of 7-methyl-3-methylene-7-octenal dibutyl acetal
[R$^1$=R$^2$=CH$_2$CH$_2$CH$_2$CH$_3$=Bu in General Formula (1)]

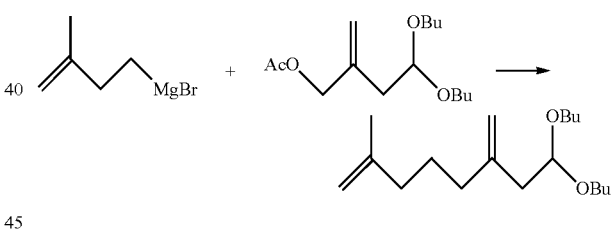

In the same manner as in Example 3 except that 0.65 g of 3-acetoxymethyl-3-butenal dibutyl acetal (90.5% GC) was used in place of 3-bromomethyl-3-butenal diethyl acetal, 0.81 g of 7-methyl-3-methylene-7-octenal dibutyl acetal (82.3% GC, quantitative yield) was produced.

7-Methyl-3-methylene-7-octenal dibutyl acetal

Colorless oil.

IR (D-ATR): v=2959, 2934, 2872, 1649, 1456, 1375, 1232, 1116, 1072, 1039 cm$^{-1}$.

$^1$H-NMR (500 MHz, CDCl$_3$): δ=0.91 (6H, t, J=7.3 Hz), 1.33-1.42 (4H, m), 1.51-1.60 (6H, m), 1.71 (3H, s), 2.00 (2H, br. t, J=7.6 Hz), 2.05 (2H, br. t, J=7.7 Hz), 2.34 (2H, d, J=5.7 Hz), 3.39-3.44 (2H, m), 3.56-3.61 (2H, m), 4.58 (1H, t, J=5.7 Hz), 4.67 (1H, br. s), 4.70 (1H, br. s) 4.81 (1H, br. s), 4.82 (1H, br. s) ppm.

$^{13}$C-NMR (125 MHz, CDCl$_3$): δ=13.88 (2C), 19.40 (2C), 22.35, 25.56, 31.93 (2C), 36.12, 37.40, 40.11, 65.34 (2C), 102.35, 109.85, 111.63, 145.29, 145.80 ppm.

GC-MS (EI, 70 eV): 41, 57 (base peak), 81, 103, 121, 135, 159, 281 [(M−H)$^+$].

Example 6: Production of 7-methyl-3-methylene-7-octenal dimethyl acetal [R¹=R²=CH₃=Me in General Formula (1)]

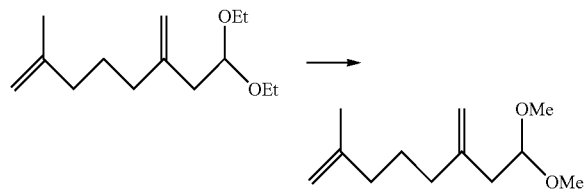

Under a nitrogen atmosphere, a mixture of 2.0 g of 7-methyl-3-methylene-7-octenal diethyl acetal (83.6% GC), 15.0 g of methanol and 0.05 g of pyridinium p-toluenesulfonate monohydrate was stirred at room temperature for 2 hours. The reaction mixture was poured in a saturated aqueous sodium hydrogen carbonate solution and extracted with n-hexane. The separated organic phase was subjected to common work-up of washing, drying and concentration to obtain 0.91 g of 7-methyl-3-methylene-7-octenal dimethyl acetal (86.6% GC, yield: 54%).

7-Methyl-3-methylene-7-octenal dimethyl acetal

Colorless oil.

IR (D-ATR): ν=3074, 2936, 2830, 1648, 1446, 1373, 1192, 1123, 1078, 1060, 888 cm$^{-1}$.

¹H-NMR (500 MHz, CDCl₃): δ=1.55-1.61 (2H, m), 1.71 (3H, s), 2.01 (2H, t, J=7.6 Hz), 2.05 (2H, t, J=7.8 Hz), 2.34 (2H, d, J=5.7 Hz), 3.32 (6H, s), 4.51 (1H, t, J=5.8 Hz), 4.67 (1H, br. s), 4.70 (1H, br. s), 4.79 (2H, br. s) ppm.

¹³C-NMR (125 MHz, CDCl₃): δ=22.35, 25.53, 35.89, 37.34, 39.20, 52.70 (2C), 103.41, 109.91, 111.86, 144.88, 145.73 ppm.

GC-MS (EI, 70 eV): 47, 75 (base peak), 109, 197 [(M−H)⁺].

Example 7: Production of 7-methyl-3-methylene-7-octenal ethylene acetal [R¹—R²=CH₂CH₂ in General Formula (1)]

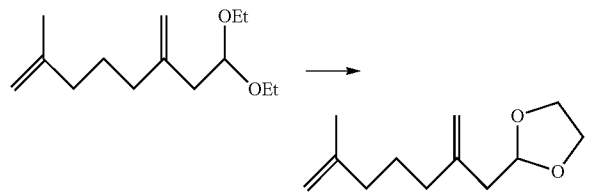

Under a nitrogen atmosphere, a mixture of 3.0 g of 7-methyl-3-methylene-7-octenal diethyl acetal (83.6% GC), 4.00 g of ethylene glycol, 0.05 g of pyridinium p-toluenesulfonate monohydrate and 12 ml of toluene was stirred and refluxed with heating, while distilling off the generated ethanol. Two hours later when the distillation was over, the reaction mixture was cooled to room temperature, then poured in water, and extracted with n-hexane. The separated organic phase was subjected to common work-up of washing, drying and concentration to obtain 2.61 g of 7-methyl-3-methylene-7-octenal ethylene acetal (83.4% GC, quantitative yield).

7-Methyl-3-methylene-7-octenal ethylene acetal

Colorless oil.

IR (D-ATR): ν=3074, 2936, 2883, 1648, 1444, 1396, 1213, 1133, 1044, 889 cm$^{-1}$.

¹H-NMR (500 MHz, CDCl₃): δ=1.55-1.62 (2H, m), 1.71 (3H, s), 2.01 (2H, t, J=7.6 Hz), 2.08 (2H, t, J=7.8 Hz), 2.38 (2H, d, J=5.2 Hz), 3.82-3.88 (2H, m), 3.94-4.01 (2H, m), 4.67 (1H, br. s-like), 4.70 (1H, br. s-like), 4.88 (2H, br. s-like), 4.97 (1H, t, J=5.2 Hz) ppm.

¹³C-NMR (125 MHz, CDCl₃): δ=22.33, 25.47, 36.09, 37.31, 40.63, 64.76 (2C), 103.60, 109.88, 112.22, 144.48, 145.70 ppm.

GC-MS (EI, 70 eV): 45, 73 (base peak), 195 [(M−H)⁺].

Example 8: Production No. 1 of 7-methyl-3-methylene-7-octenal (2)

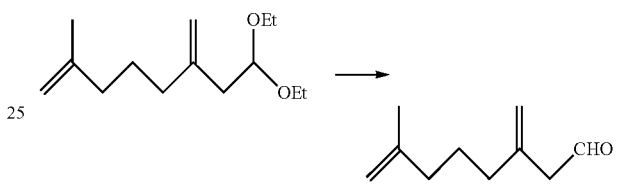

Under a nitrogen atmosphere, 2.00 g of 7-methyl-3-methylene-7-octenal diethyl acetal (93% GC) and 6.00 g of a mixture of water, acetic acid and formic acid at a weight ratio of 10:5:1 were stirred at 50° C. for 1 hour and at 60° C. for 4 hours. The reaction mixture was cooled and diluted with toluene. The separated organic phase was subjected to common work-up of washing, drying and concentration to obtain, as a crude product, 1.58 g of a mixture (65% GC, total yield of three compounds: 77%) of 7-methyl-3-methylene-7-octenal, Z-3,7-dimethyl-2,7-octadienal and E-3,7-dimethyl-2,7-octadienal at a ¹H-NMR integral area ratio of 80.9:7.6:11.5.

7-Methyl-3-methylene-7-octenal

Yellowish liquid

IR (D-ATR): ν=3075, 2970, 2937, 1725, 1675, 1647, 1445, 1375, 890 cm$^{-1}$.

¹H-NMR (500 MHz, CDCl₃): δ=1.55-1.63 (2H, m), 1.71 (3H, s), 2.01 (2H, t, J=7.7 Hz), 2.06 (2H, t, J=7.7 Hz), 3.09 (2H, d-like, J=2.7 Hz), 4.68 (1H, br. s), 4.2 (1H, br. s), 4.92 (1H, br. s), 5.05 (1H, br. s), 9.64 (1H, t, J=2.7 Hz) ppm.

¹³C-NMR (125 MHz, CDCl₃): δ=22.26, 25.09, 36.19, 37.11, 50.95, 110.17, 114.78, 140.54, 145.28, 199.99 ppm.

GC-MS (EI, 70 eV): 41 (base peak), 53, 67, 81, 93, 108, 119, 137, 152 (M⁺).

Example 9: Production No. 2 of 7-methyl-3-methylene-7-octenal (2)

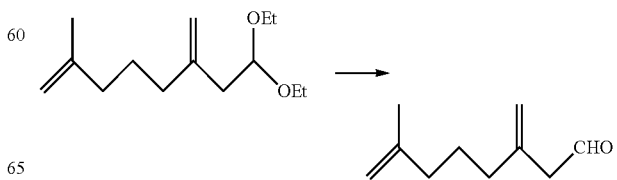

Under a nitrogen atmosphere, a mixture of 20.0 g of 7-methyl-3-methylene-7-octenal diethyl acetal (83% GC), 10 ml of tetrahydrofuran and 10 ml of toluene was subjected to addition of 50 g of 10% hydrochloric acid, and stirred at room temperature for 8 hours and at 40° C. for 1 hour. The reaction mixture was cooled, and then the organic phase was separated. The organic phase having a reaction conversion [=100×(product GC %)/{(product GC %+material GC %)}] of 70% contained 7-methyl-3-methylene-7-octenal, Z-3,7-dimethyl-2,7-octadienal and E-3,7-dimethyl-2,7-octadienal at a GC % ratio of 82.8:7.3:9.9. The organic phase was not further purified and was subjected to the next step.

Example 10: Production No. 3 of 7-methyl-3-methylene-7-octenal (2)

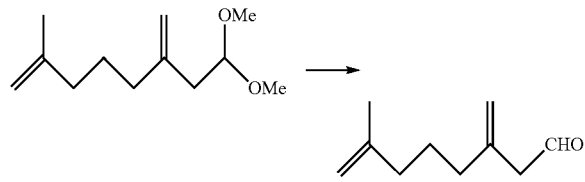

Under a nitrogen atmosphere, a mixture of 0.50 g of 7-methyl-3-methylene-7-octenal dimethyl acetal (87% GC), 1.8 g of oxalic acid dihydrate, 2 ml of tetrahydrofuran and 4 ml of water was stirred at room temperature for 6 hours. The reaction mixture was cooled and then diluted with n-hexane. The separated organic phase was subjected to common work-up of washing, drying and concentration to obtain, as a crude product, 0.24 g of a mixture (87.7% GC, total yield of three compounds: 66%) of 7-methyl-3-methylene-7-octenal, Z-3,7-dimethyl-2,7-octadienal and E-3,7-dimethyl-2,7-octadienal at a GC % ratio of 83.1:6.6:10.3. The obtained target compound was identical with the target compound in Example 8.

Example 11: Production of 7-methyl-3-methylene-7-octenol (3)

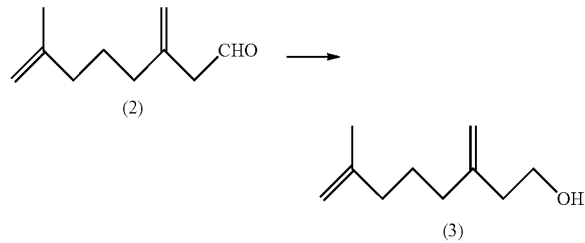

Under a nitrogen atmosphere, a mixture of 3.50 g of sodium borohydride, 2 ml of a 20% aqueous sodium hydroxide solution and 60 ml of water was cooled on ice and subjected to dropwise addition, at 10° C. or less over 20 minutes, of the organic phase containing 7-methyl-3-methylene-7-octenal (2) and being obtained in Example 9. The reaction mixture was stirred for 24 hours, and then the organic phase was separated. The separated organic phase was subjected to common work-up of washing, drying and concentration to obtain 13.45 g of a crude product. The crude product contained 49.1% GC (conversion yield: 49%) of the target compound 7-methyl-3-methylene-7-octenol and 24.8% GC (converted yield: 20.3%) of 7-methyl-3-methylene-7-octenal diethyl acetal, which was the starting material in Example 9. The crude product was separated and purified by silica gel column chromatography to obtain 3.66 g of the starting material 7-methyl-3-methylene-7-octenal diethyl acetal (83.1% GC, 2-step recovery yield from Example 9: 18%) and two fractions: 5.00 g (97.7% GC) and 0.84 g (95.2% GC) of the target compound 7-methyl-3-methylene-7-octenol. The 2-step yield of the total of the two fractions of 7-methyl-3-methylene-7-octenol was 54% from Example 9, and the 2-step yield of 7-methyl-3-methylene-7-octenol in consideration of material recovery was 66% from Example 9.

7-Methyl-3-methylene-7-octenol

Yellowish oil

IR (D-ATR): ν=3336, 3074, 2936, 1647, 1445, 1374, 1046, 887 cm$^{-1}$.

$^1$H-NMR (500 MHz, CDCl$_3$): δ=1.54-1.64 (2H, m), 1.63 (1H, OH, t-like, J=ca. 5 Hz), 1.71 (3H, s), 1.97-2.07 (4H, m), 2.29 (2H, t-like, J=6.4 Hz), 3.70 (2H, q-like, J=ca. 6 Hz), 4.67 (1H, br. s), 4.70 (1H, br. s), 4.82 (1H, br. s), 4.86 (1H, br. s) ppm.

$^{13}$C-NMR (125 MHz, CDCl$_3$): δ=22.31, 25.53, 35.26, 37.30, 39.09, 60.31, 109.97, 111.59, 145.59, 145.91 ppm.

GC-MS (EI, 70 eV): 41, 55, 68 (base peak), 81, 93, 109, 121, 139, 154 (M$^+$).

GC-MS (CI, isobutane): 69, 81, 95, 111, 125, 137, 155 [(M+H)$^+$].

Example 12: Production of 7-methyl-3-methylene-7-octenyl propionate [R$^3$=CH$_2$CH$_3$ in General Formula (4)]

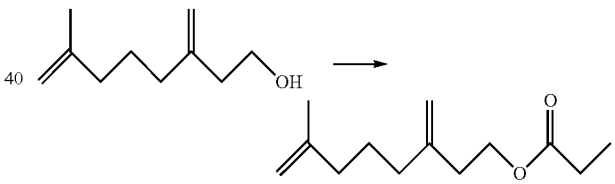

Under a nitrogen atmosphere, a mixture of 5.45 g of 7-methyl-3-methylene-7-octenol (88.3% GC), 10.0 g of pyridine and 30 ml of tetrahydrofuran was subjected to addition of 4.80 g of propionic anhydride. The reaction mixture was refluxed with heating and stirring for 5 hours, and then subjected to addition of a saturated aqueous sodium hydrogen carbonate solution to stop the reaction. The separated organic phase was subjected to common work-up of washing, drying and concentration to obtain 7.44 g of a crude product of 7-methyl-3-methylene-7-octenyl propionate. The crude product was distilled under reduced pressure to obtain 5.25 g of the target compound 7-methyl-3-methylene-7-octenyl propionate (95.5% GC, yield including initial distillate having 87.7% GC: 91%).

7-Methyl-3-methylene-7-octenyl propionate

Colorless oil

Boiling point: 80° C./399 Pa.

IR (D-ATR): ν=3076, 2981, 2938, 1739, 1648, 1462, 1376, 1349, 1273, 1181, 1084, 1016, 889 cm-1.

$^1$H-NMR (500 MHz, CDCl$_3$): δ=1.12 (3H, t, J=7.6 Hz), 1.53-1.61 (2H, m), 1.71 (3H, s), 1.97-2.06 (4H, m), 2.31 (2H, q, J=7.6 Hz), 2.33 (2H, t-like, J=7 Hz), 4.17 (2H, t, J=7.1 Hz), 4.67 (1H, s-like), 4.70 (1H, s-like), 4.77 (1H, s-like), 4.81 (1H, s-like) ppm.

$^{13}$C-NMR (125 MHz, CDCl$_3$): δ=9.10, 22.32, 25.51, 27.56, 34.95, 35.86, 37.29, 62.73, 109.96, 111.18, 145.44, 145.60, 174.41 ppm.

GC-MS (EI, 70 eV): 29, 41, 57 (base peak), 68, 79, 93, 107, 121, 136, 210 (M$^+$).

Example 13: Production of 7-methyl-3-methylene-7-octenyl senecioate [R$^3$=CH:C(CH$_3$)$_2$ in General Formula (4)]

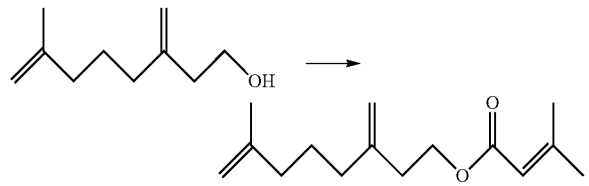

Under a nitrogen atmosphere, a mixture of 4.00 g of 7-methyl-3-methylene-7-octenol (95.2% GC), 10.0 g of methyl senecioate and 0.5 ml of titanium(IV) isopropoxide was heated, while gradually increasing the bath temperature from 80° C. to 155° C. and distilling off the generated methanol. Two hours later when the distillation of methanol was over as a result of continuous heating, the vapor temperature increased to 136° C., which was the boiling point of methyl senecioate. The reaction mixture was cooled, and then was directly distilled under reduced pressure to recover excess methyl senecioate. Then 2.89 g of the target compound 7-methyl-3-methylene-7-octenyl senecioate (96.6% GC, yield including initial distillate having 84.7% GC: 56%) was obtained.

7-Methyl-3-methylene-7-octenyl senecioate
Colorless oil
Boiling point: 94-95° C./399 Pa.
IR (D-ATR): ν=3075, 2969, 2937, 2916, 1720, 1651, 1446, 1377, 1348, 1272, 1228, 1147, 1080, 1000, 889, 851 cm$^{-1}$.

$^1$H-NMR (500 MHz, CDCl$_3$): δ=1.54-1.61 (2H, m), 1.70 (3H, s), 1.88 (3H, d, J=1.3 Hz), 2.02 (4H, quint-like, J=ca. 7 Hz), 2.15 (3H, d, J=1.1 Hz), 2.35 (2H, t-like, J=7 Hz), 4.19 (2H, t, J=7.1 Hz), 4.66 (1H, s-like), 4.70 (1H, s-like), 4.79 (1H, s-like), 4.81 (1H, s-like), 5.66 (1H, septet, J=1.3 Hz) ppm.

$^{13}$C-NMR (125 MHz, CDCl$_3$): δ=20.14, 22.32, 25.52, 27.33, 35.01, 35.69, 37.30, 62.02, 109.94, 111.07, 115.99, 145.61, 145.63, 156.54, 166.61 ppm.

GC-MS (EI, 70 eV): 29, 41, 55, 68, 83 (base peak), 95, 107, 121, 136, 236 (M$^+$).

Example 14: Production of 7-methyl-3-methylene-7-octenyl acetate [R$^3$=CH$_3$ in General Formula (4)]

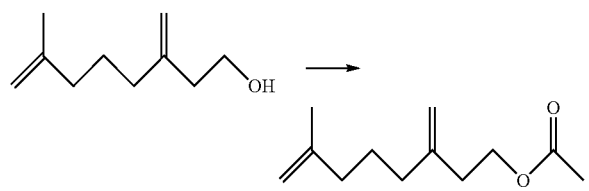

Under a nitrogen atmosphere, a mixture of 5.00 g of 7-methyl-3-methylene-7-octenol (95.2% GC), 10.0 g of pyridine and 4.00 g of acetic anhydride was stirred at room temperature for 3 hours. The reaction mixture was poured in cold water and extracted with diethyl ether. The crude product obtained by common washing, drying and concentration was distilled under reduced pressure to obtain 5.82 g of the target compound 7-methyl-3-methylene-7-octenyl acetate (96.4% GC, yield including initial distillate having 91.9% GC: 96%).

7-Methyl-3-methylene-7-octenyl acetate
Colorless oil
Boiling point: 56-58° C./399 Pa.
IR (D-ATR): ν=3075, 2967, 2937, 2866, 1743, 1648, 1445, 1365, 1237, 1036, 889 cm-1.

$^1$H-NMR (500 MHz, CDCl$_3$): δ=1.53-1.60 (2H, m), 1.98-2.04 (4H, m), 2.03 (3H, s), 2.33 (2H, t-like, J=7.1 Hz), 4.16 (2H, t, J=7.1 Hz), 4.66 (1H, s-like), 4.70 (1H, s-like), 4.77 (1H, s-like), 4.81 (1H, s-like) ppm.

$^{13}$C-NMR (125 MHz, CDCl$_3$): δ=20.93, 22.32, 25.48, 34.86, 35.65, 37.28, 62.88, 109.97, 111.17, 145.38, 145.58, 171.02 ppm.

GC-MS (EI, 70 eV): 29, 43 (base peak), 56, 69, 81, 95, 109, 124, 137.

Example 15: Production No. 1 of 3,7-dimethyl-2,7-octadienal (5)

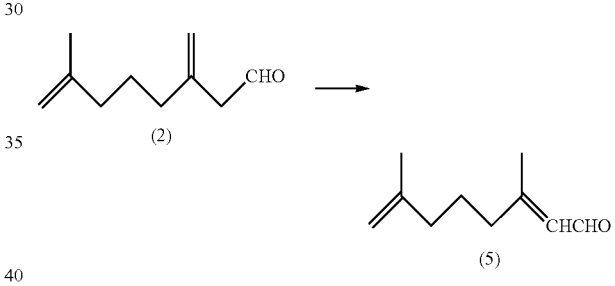

Under a nitrogen atmosphere, a mixture of 1.00 g of pyridine and 5.00 g of toluene with 1.00 g of a mixture (65.6% GC, containing 37.3% toluene) of 7-methyl-3-methylene-7-octenal, Z-3,7-dimethyl-2,7-octadienal and E-3,7-dimethyl-2,7-octadienal at a ratio of 76:9:16 was refluxed with heating and stirring for 8 hours. The reaction mixture was cooled, then poured in a diluted hydrochloric acid, and extracted with n-hexane. The organic phase was subjected to common work-up of washing, drying and concentration to obtain, as a crude product, 0.80 g of a mixture (86.2% GC, quantitative yield) of Z-3,7-dimethyl-2,7-octadienal and E-3,7-dimethyl-2,7-octadienal at a ratio of 35:65.

3,7-Dimethyl-2,7-octadienal
Isomer ratio Z:E=35.0:65.0
Yellowish oil
IR (D-ATR): ν=3074, 2938, 2861, 1675, 1444, 1376, 1195, 1122, 887 cm$^{-1}$.

$^1$H-NMR (500 MHz, CDCl$_3$): δ=1.62-1.69 (2H, m, Z & E), 1.70 (3H, s-like, Z & E), 1.96 (3×0.35H, d, J=1.2 Hz, Z), 2.00-2.06 (2H, m, Z & E), 2.15 (3×0.65H, d, J=1.2 Hz, E), 2.19 (2×0.65H, br. t, J=7.7 Hz, E), 2.55 (2×0.35H, dd, J=7.6, 8.1 Hz, Z), 4.66-4.74 (2H, m, Z & E), 5.86-5.88 (2H, m, Z & E), 9.93 (0.35H, d, J=8 Hz, Z), 9.84 (0.65H, d, J=8 Hz, E) ppm.

$^{13}$C-NMR (125 MHz, CDCl$_3$): δ=17.47 (Z & E), 22.19 (Z & E), 24.85 (E), 26.33 (Z), 31.89 (Z), 37.04 (E), 37.13 (Z), 39.94 (E), 110.50 (E), 110.69 (Z), 127.34 (E), 128.53 (Z), 144.56 (E), 144.79 (Z), 163.94 (E), 164.34 (Z), 190.67 (Z), 191.22 (E) ppm.

GC-MS (EI, 70 eV): (Z)-isomer: 41, 53, 67, 84 (base peak), 95, 109, 119, 137, 152 (M$^+$); (E)-isomer: 41 (base peak), 53, 67, 81, 95, 109, 123, 137, 152 (M$^+$).

GC-MS (CI, isobutane): (Z)-isomer: 71, 95, 109 (base peak), 135, 153 [(M+H)$^+$]; (E)-isomer: 71, 95, 109 (base peak), 135, 153 [(M+H)$^+$].

Example 16: Production No. 2 of 3,7-dimethyl-2,7-octadienal (5)

Under a nitrogen atmosphere, a mixture of 2.00 g of 1,8-diazabicyclo[5.4.0]-7-undecene and 80 ml of toluene with 62.3 g of a mixture (52.4% GC, containing 37.1% toluene) of 7-methyl-3-methylene-7-octenal, Z-3,7-dimethyl-2,7-octadienal and E-3,7-dimethyl-2,7-octadienal at a ratio of 39:23:38 was stirred at room temperature for 3 hours. The reaction mixture contained a mixture of Z-3,7-dimethyl-2,7-octadienal and E-3,7-dimethyl-2,7-octadienal at a ratio of 37:63. Components of the reaction mixture were identical with those in Example 15 except for the isomer ratio.

Example 17: Production No. 3 of 3,7-dimethyl-2,7-octadienal (5)

Under a nitrogen atmosphere, a mixture of 0.1 g of triethylamine and 1 ml of tetrahydrofuran with 200 mg of a mixture (87.3% GC) of 7-methyl-3-methylene-7-octenal, Z-3,7-dimethyl-2,7-octadienal and E-3,7-dimethyl-2,7-octadienal at a GC % ratio of 55:16:29 was stirred at room temperature for 18 hours. The reaction mixture contained a mixture of Z-3,7-dimethyl-2,7-octadienal and E-3,7-dimethyl-2,7-octadienal at a ratio of 18:82. Components of the reaction mixture were identical with those in Example 15 except for the isomer ratio.

Example 18: Production No. 4 of 3,7-dimethyl-2,7-octadienal (5)

Under a nitrogen atmosphere, a mixture of 2.0 g of triethylamine and 100 ml of tetrahydrofuran with 28.5 g of a mixture (87.3% GC) of 7-methyl-3-methylene-7-octenal, Z-3,7-dimethyl-2,7-octadienal and E-3,7-dimethyl-2,7-octadienal at a ratio of 55:16:29 was stirred at room temperature for 18 hours. The reaction mixture contained a mixture of Z-3,7-dimethyl-2,7-octadienal and E-3,7-dimethyl-2,7-octadienal at a ratio of 19:81. Components of the reaction mixture were identical with those in Example 15 except for the isomer ratio.

Example 19: Production No. 1 of 3,7-dimethyl-2,7-octadienol (6)

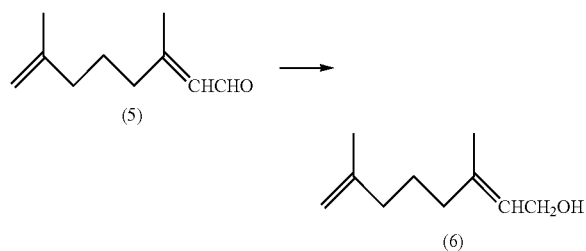

Under a nitrogen atmosphere, a mixture of 22.0 g of sodium borohydride, 10 ml of a 15% aqueous sodium hydroxide solution and 300 ml of water was stirred on ice, and a mixture of 500 ml of tetrahydrofuran with 128.4 g of a mixture (68.9% GC) of Z-3,7-dimethyl-2,7-octadienal and E-3,7-dimethyl-2,7-octadienal at a ratio of 36:64 was added dropwise at 12° C. or less over 1 hour. The reaction mixture was stirred on ice for 40 minutes and at room temperature for 1 hour. Then the organic phase was separated, and the aqueous phase was extracted with diethyl ether. The combined organic phase was subjected to common work-up of washing, drying and concentration to obtain a crude product. The crude product was a mixture (74.8% GC, quantitative yield) of Z-3,7-dimethyl-2,7-octadienol and E-3,7-dimethyl-2,7-octadienol at a ratio of 33:67. The crude product was not further purified and was subjected to the next step.

3,7-Dimethyl-2,7-octadienol

Isomer ratio Z:E=33:67.

Yellowish oil

IR (D-ATR): ν=3336, 3074, 2968, 2935, 1649, 1444, 1375, 999, 886 cm$^{-1}$.

$^1$H-NMR (500 MHz, CDCl$_3$): δ=1.45 (1H, br, Z & E), 1.48-1.59 (2H, m, Z & E), 1.66 (3×0.64H, br. s, E), 1.70 (3H, br. s, Z & E), 1.73 (3×0.33H, br. s, Z), 1.95-2.03 (4×0.67H+2×0.33H, m, Z & E), 2.06 (2×0.33H, br. t, J=8 Hz, Z), 4.10 (0.33H, br. s, Z), 4.11 (0.33H, br. s, Z), 4.13 (0.67H, br. s, E), 4.15 (0.67H, br. s, E), 4.63-4.74 (2H, m, Z & E), 5.38-5.44 (1H, m, Z & E) ppm.

$^{13}$C-NMR (125 MHz, CDCl$_3$): δ=16.13 (E), 22.34 (E+Z), 23.34 (Z), 25.53 (E), 25.99 (Z), 31.38 (Z), 37.29 (E), 37.39 (Z), 39.04 (E), 58.97 (Z), 59.29 (E), 109.86 (E), 109.95 (Z), 123.39 (E), 124.27 (Z), 139.62 (E), 139.95 (Z), 145.55 (Z), 145.71 (E) ppm.

GC-MS (EI, 70 eV): (Z)-isomer: 41, 55, 69 (base peak), 83, 96, 109, 121, 136, 154 (M$^+$); (E)-isomer: 41, 55, 69 (base peak), 83, 96, 109, 121, 136, 154 (M$^+$).

Example 20: Production No. 2 of 3,7-dimethyl-2,7-octadienol (6)

Under a nitrogen atmosphere, a mixture of 5.0 g of sodium borohydride, 5.0 g of a 20% aqueous sodium hydroxide solution and 50 ml of water was stirred on ice, and a mixture of 100 ml of ethanol with the reaction mixture containing Z-3,7-dimethyl-2,7-octadienal and E-3,7-dimethyl-2,7-octadienal at a ratio of 37:63 and being obtained in Example 16 was dropwise added thereto over 20 minutes. The reaction mixture was stirred at room temperature for 16 hours, then the organic phase was separated, and the aqueous phase was extracted with diethyl ether. The combined organic phase was subjected to common work-up of washing, drying and concentration to obtain a crude product. The crude product was a mixture (69.2% GC, quantitative yield) of Z-3,7-dimethyl-2,7-octadienol and E-3,7-dimethyl-2,7-octadienol at a ratio of 37:63. Components of the mixture were identical with those in Example 19 except for the isomer ratio.

Example 21: Production No. 3 of 3,7-dimethyl-2,7-octadienol (6)

Under a nitrogen atmosphere, the reaction mixture containing Z-3,7-dimethyl-2,7-octadienal and E-3,7-dimethyl-2,7-octadienal at a ratio of 19:81 and being obtained in Example 18 was stirred on ice, and a mixture of 5.0 g of sodium borohydride, 0.4 ml of a 20% aqueous sodium hydroxide solution and 100 ml of water was dropwise added thereto at 12° C. or less over 20 minutes. The reaction mixture was stirred on ice for 140 minutes, then a saturated salt solution was added thereto, and the organic phase was separated. The organic phase was subjected to common work-up of washing, drying and concentration to obtain a crude product. The crude product was a mixture (78.8% GC, yield: 94%) of Z-3,7-dimethyl-2,7-octadienol and E-3,7-dimethyl-2,7-octadienol at a ratio of 19:81. Components of the mixture were identical with those in Example 19 except for the isomer ratio.

Example 22: Production No. 1 of 3,7-dimethyl-2,7-octadienyl propionate [R³=CH₂CH₃ in General Formula (7)]

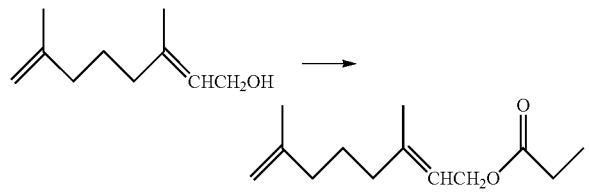

Under a nitrogen atmosphere, a mixture of 90.0 g of pyridine and 700 ml of t-butyl methyl ether with 122 g of the mixture (74.8% GC) of Z-3,7-dimethyl-2,7-octadienol and E-3,7-dimethyl-2,7-octadienol at a ratio of 33:67 obtained in Example 19 was stirred on ice, and 55.0 g of propionyl chloride was dropwise added thereto at 12° C. or less over 50 minutes. The reaction mixture was stirred at room temperature for 14 hours, then cooled on ice, and a saturated aqueous sodium hydrogen carbonate solution was added thereto. The separated organic phase was subjected to common work-up of washing, drying and concentration to obtain 144.16 g of a crude product. The crude product was a mixture of the target compounds Z-3,7-dimethyl-2,7-octadienyl propionate and E-3,7-dimethyl-2,7-octadienyl propionate at a ratio of 33:67. The crude product was fractionated under vacuum distillation to obtain 58.56 g of a mixture (87.6 to 95.5% GC, an isomer ratio Z:E of 42:58 to 18:84, yield including initial distillate with low purity: 51%) of the target compounds Z-3,7-dimethyl-2,7-octadienyl propionate and E-3,7-dimethyl-2,7-octadienyl propionate.
3,7-Dimethyl-2,7-octadienyl propionate (95.5% GC)
  Isomer ratio Z:E=29:71.
  Yellowish oil
  Boiling point: 81-85° C./399 Pa.
  IR (D-ATR): ν=3073, 2971, 2939, 1738, 1650, 1462, 1377, 1180, 1081, 887 cm⁻¹.
  ¹H-NMR (500 MHz, CDCl₃): δ=1.13 (3×0.29H, t, J=7.6 Hz, Z), 1.13 (3×0.71H, t, J=7.6 Hz), 1.69 (3H, br. s, Z & E), 1.70 (3H, br. s, Z & E), 1.96-2.03 (4×0.71+2×0.29H, m, Z & E), 2.08 (2×0.29H, br. t, J=7.7 Hz, Z), 2.31 (2×0.29H, q, J=7.6 Hz, Z), 2.32 (2×0.71H, q, J=7.6 Hz, E), 4.55 (0.29H, br. s, Z), 4.56 (0.29H, br. s, Z), 4.58 (0.71H, br. s, E), 4.59 (0.71H, br. s, E), 4.66 (2H, br. s, Z & E), 4.70 (2H, br. s, Z & E), 5.31-5.38 (1H, m, Z & E) ppm.
  ¹³C-NMR (125 MHz, CDCl₃): δ=9.10 (Z & E), 16.31 (E), 22.32 (Z & E), 23.39 (Z), 25.44 (E), 25.97 (Z), 27.57 (Z & E), 31.57 (Z), 37.24 (E), 37.40 (Z), 39.01 (E), 60.87 (Z), 61.20 (E), 109.94 (E), 109.98 (Z), 118.48 (E), 119.23 (Z), 142.05 (E), 142.61 (Z), 145.47 (Z), 145.62 (E), 174.46 (Z), 174.47 (E) ppm.
  GC-MS (EI, 70 eV): (Z)-isomer: 29, 41, 57 (base peak), 69, 81, 93, 107, 121, 136, 154, 167, 181, 195; (E)-isomer: 29, 41, 57 (base peak), 69, 81, 93, 107, 121, 136, 154, 167, 181, 195.

Example 23: Production No. 2 of 3,7-dimethyl-2,7-octadienyl propionate [R³=CH₂CH₃ in General Formula (7)]

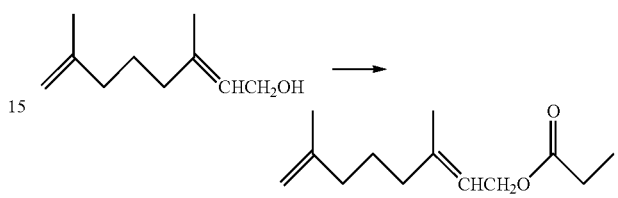

Under a nitrogen atmosphere, a mixture of 26.2 g of pyridine and 200 ml of t-butyl methyl ether with 34.1 g of the mixture of Z-3,7-dimethyl-2,7-octadienol and E-3,7-dimethyl-2,7-octadienol at a ratio of 19:81 obtained in Example 21 was stirred on ice, and 25.6 g of propionyl chloride was dropwise added thereto at 20° C. or less over 20 minutes. The reaction mixture was stirred at room temperature for 2.5 hours and then cooled on ice, and a saturated aqueous sodium hydrogen carbonate solution was added thereto. The separated organic phase was subjected to common work-up of washing, drying and concentration to obtain 43.90 g of a crude product. The crude product was fractionated by vacuum distillation to obtain 31.90 g of a mixture (95.8% GC, a isomer ratio Z:E=19:81, yield including initial distillate with low purity: 87%) of the target compounds Z-3,7-dimethyl-2,7-octadienyl propionate and E-3,7-dimethyl-2,7-octadienyl propionate. Components of the mixture were identical with those in Example 22 except for the isomer ratio.

Example 24: Simultaneous Production of a Mixture of 7-methyl-3-methylene-7-octenal (2) and 3,7-dimethyl-2,7-octadienal (5)

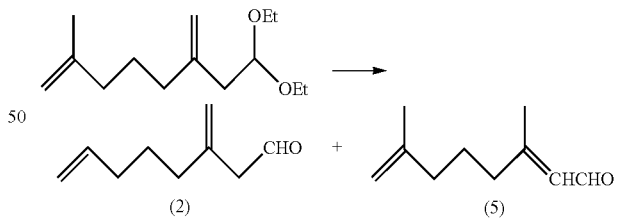

First, 10.0 g of 7-methyl-3-methylene-7-octenal diethyl acetal (83.6% GC) and 30 g of a mixture of water, acetic acid and formic acid at a weight ratio of 10:5:1 were stirred at 70 to 80° C. for 8 hours. The reaction mixture was cooled, then diluted with toluene, and washed, and then the organic phase was separated. The organic phase contained a mixture of the target compounds 7-methyl-3-methylene-7-octenal, Z-3,7-dimethyl-2,7-octadienal and E-3,7-dimethyl-2,7-octadienal at a GC area ratio of 33:26:41. Components of the mixture were the same as those in Example 8 and Example 15 although the isomer ratio was different. The organic phase was not further purified and was subjected to the next step.

Example 25: Simultaneous Production of a Mixture of 7-methyl-3-methylene-7-octenol (3) and 3,7-dimethyl-2,7-octadienol (6)

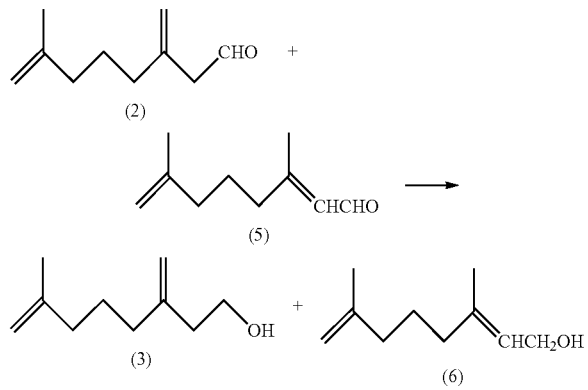

Under a nitrogen atmosphere, a mixture of 1.50 g of sodium borohydride, 50 ml of a 20% aqueous sodium hydroxide solution and 50 ml of water was stirred on ice, and a mixture of 50 ml of ethanol with the mixture of 7-methyl-3-methylene-7-octenal, Z-3,7-dimethyl-2,7-octadienal and E-3,7-dimethyl-2,7-octadienal at a GC area ratio of 33:26:41 obtained in Example 24 was dropwise added thereto at 15° C. or less over 30 minutes. The reaction mixture was warmed to room temperature and stirred for 16 hours, and then the organic phase was separated. The organic phase was subjected to common work-up of washing, drying and concentration to obtain 5.63 g of a crude product. The crude product was a mixture (71.9% GC, yield: 71%) of the target compounds 7-methyl-3-methylene-7-octenol, Z-3,7-dimethyl-2,7-octadienol and E-3,7-dimethyl-2,7-octadienol at a GC area ratio of 32:28:41. Components of the mixture were the same as those in Example 11 and Example 19 although the isomer ratio is different. The crude product was not further purified and was subjected to the next step.

Example 26: Simultaneous Production of a Mixture of 7-methyl-3-methylene-7-octenyl propionate [$R^3$=$CH_2CH_3$ in General Formula (4)] and 3,7-dimethyl-2,7-octadienyl propionate [$R^3$=$CH_2CH_3$ in General Formula (7)]

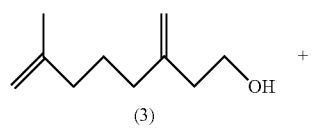

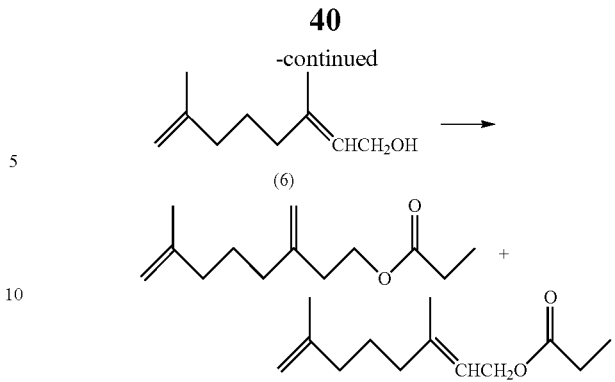

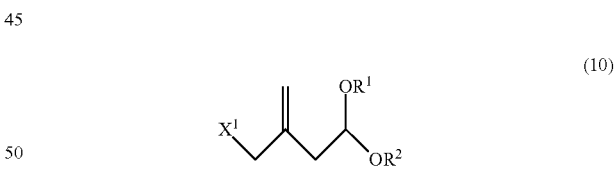

Under a nitrogen atmosphere, a mixture of 20.0 g of pyridine and 20.0 g of tetrahydrofuran with 5.48 g of the mixture (71.9% GC) of 7-methyl-3-methylene-7-octenol, Z-3,7-dimethyl-2,7-octadienol and E-3,7-dimethyl-2,7-octadienol at a ratio 32:28:41 obtained in Example 25 was stirred on ice, and 4.00 g of propionyl chloride was added thereto. The reaction mixture was stirred on ice for 2 hours and at room temperature for 17 hours, and water was added thereto to stop the reaction. Hexane was added thereto, and the separated organic phase was subjected to common work-up of washing, drying and concentration to obtain 7.15 g of a crude product. The crude product was a mixture of the target compounds 7-methyl-3-methylene-7-octenyl propionate, Z-3,7-dimethyl-2,7-octadienyl propionate and E-3,7-dimethyl-2,7-octadienyl propionate at a ratio of 30:27:43. The crude product was distilled under reduced pressure to obtain 5.03 g of a mixture (89.3% GC, yield including initial distillate having 54.9% GC: 89%) of the target compounds 7-methyl-3-methylene-7-octenyl propionate, Z-3,7-dimethyl-2,7-octadienyl propionate and E-3,7-dimethyl-2,7-octadienyl propionate at a ratio of 30:27:44.

Mixture of 7-methyl-3-methylene-7-octenyl propionate, Z-3,7-dimethyl-2,7-octadienyl propionate and E-3,7-dimethyl-2,7-octadienyl propionate at a ratio of 30:27:44

Boiling point: 75° C./332 Pa.

Components of the mixture were the same as those in Example 12 and Example 22 although the isomer ratio was different.

The invention claimed is:

1. A 3-acyloxymethyl-3-butenal acetal compound of General Formula (10):

$$\text{(10)}$$

wherein $R^1$ and $R^2$, which may be the same or different, are each an alkyl group having 1 to 6 carbon atoms, or are bonded to each other to form a divalent alkylene group having 2 to 12 carbon atoms, and $X^1$ is an acyloxy group having 1 to 6 carbon atoms.

* * * * *